US012637487B2

(12) United States Patent
Liu et al.

(10) Patent No.: US 12,637,487 B2
(45) Date of Patent: May 26, 2026

(54) COMBINATION PRODUCT COMPRISING DICYCLOPLATIN AND PREPARATION METHOD AND USE THEREOF

(71) Applicant: MEDONCARE PHARMACEUTICAL CO., LTD., Changsha (CN)

(72) Inventors: Xiaozhong Liu, Changsha (CN); Xiong Li, Changsha (CN); Qifeng Jin, Changsha (CN); Hexiao Zheng, Changsha (CN)

(73) Assignee: MEDONCARE PHARMACEUTICAL CO., LTD., Changsha (CN)

( * ) Notice: Subject to any disclaimer, the term of this patent is extended or adjusted under 35 U.S.C. 154(b) by 116 days.

(21) Appl. No.: 16/765,024

(22) PCT Filed: Nov. 19, 2018

(86) PCT No.: PCT/CN2018/116213
§ 371 (c)(1),
(2) Date: May 18, 2020

(87) PCT Pub. No.: WO2019/101040
PCT Pub. Date: May 31, 2019

(65) Prior Publication Data

US 2020/0361973 A1 Nov. 19, 2020

(30) Foreign Application Priority Data

Nov. 21, 2017 (CN) ........................ 201711164023.6

(51) Int. Cl.
*A61P 29/00* (2006.01)
*A61P 31/18* (2006.01)
*C07F 15/00* (2006.01)
*A61K 45/06* (2006.01)

(52) U.S. Cl.
CPC .......... *C07F 15/0013* (2013.01); *A61P 29/00* (2018.01); *A61P 31/18* (2018.01); *A61K 45/06* (2013.01)

(58) Field of Classification Search
CPC ............................ C07F 15/0013; A61P 29/00
See application file for complete search history.

(56) References Cited

U.S. PATENT DOCUMENTS

2002/0136763 A1 9/2002 Demopoulos et al.
2011/0206638 A1 8/2011 Choi

FOREIGN PATENT DOCUMENTS

| | | |
|---|---|---|
| CN | 1311183 | 9/2001 |
| CN | 104127402 | 11/2014 |
| CN | 104127402 A | 11/2014 |
| CN | 106132408 | 11/2016 |
| CN | 108697093 | 10/2018 |
| EP | 1186610 A1 | 3/2002 |
| WO | 2016/164040 A1 | 10/2016 |
| WO | 2016/172393 | 10/2016 |
| WO | 2016/187191 | 11/2016 |
| WO | 2016/205782 A1 | 12/2016 |
| WO | 2016/210418 | 12/2016 |

OTHER PUBLICATIONS

Sciuto et al (J Nucl Med, 2002; 43:79-86) (Year: 2002).*
Li et al (PLoS One, 2012; 7(11):e48994, pp. 1-13) (Year: 2012).*
Giaccone (Drugs, 2000; 59(Suppl 4):9-17) (Year: 2000).*
International Search Report for PCT/CN2018/116213 mailed Feb. 3, 2019, 10 pages.
Extended European Search Report in corresponding EP Application No. 18880461.1, dated Jul. 30, 2021.

* cited by examiner

*Primary Examiner* — Rayna Rodriguez
(74) *Attorney, Agent, or Firm* — Nixon & Vanderhye, PC

(57) ABSTRACT

The present invention relates to the compositions containing dicycloplatin, pharmaceutical use of the compositions in the treatment and/or prevention of pain, inflammation and virus-related diseases, and methods of preparing the compostions thereof.

11 Claims, 4 Drawing Sheets

COMBINATION PRODUCT COMPRISING DICYCLOPLATIN AND PREPARATION METHOD AND USE THEREOF

This application is the U.S. national phase of International Application No. PCT/CN2018/116213 filed Nov. 19, 2018 which designated the U.S. and claims priority to CN patent application Ser. No. 20/171,1164023.6 filed Nov. 21, 2017, the entire contents of each of which are hereby incorporated by reference.

FIELD OF THE INVENTION

The present invention relates to combination products containing dicycloplatin, use of the combination products in the treatment and/or prevention of pain, inflammation and viral infection related diseases, and preparation methods of the combination products.

BACKGROUND TECHNOLOGY

Since the antitumor effect of cis-dichlorodiamine platinum was discovered (Rosenberg et al. *Nature,* 1965, 205: 698; *Nature,* 1972, 222: 385), cisplatin has been widely used as an antitumor drug in clinical medicine. Although these drugs have therapeutic effects on cancers, such as urogenital cancer, nasopharyngeal cancer, cephalosporin round cancer, and lung cancer, the drugs are toxic and may cause serious side effects. The search for high-efficiency antitumor drugs with low toxicity and broad spectrum of antitumor activity from platinum analogues has been a research focus in the field of antitumor drugs for the past few decades.

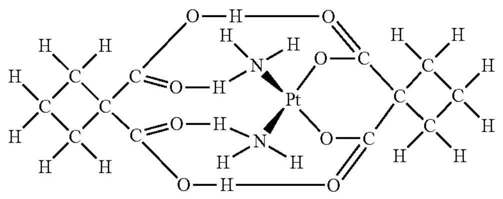

Structure of dicycloplatin

Dicycloplatin (DCP) is a co-crystal compound formed by carboplatin (CBP) and 1,1-cyclobutane-dicarboxylic acid (CBDCA) through hydrogen bonding. According to CN1311183A and corresponding academic reports, dicyloplatin has broad spectrum of antitumor activity, high efficiency, low toxicity, low resistance, low cross-resistance, and good penetrability etc. Chinese patent application CN00124864.2 shows that dicyloplatin has significant effects on head and neck cancer, nasopharyngeal cancer, breast cancer, lung cancer, liver cancer, pancreatic cancer, gastric cancer, bowel cancer, and lymphoma etc. At the same time, it has good effects on multiple indications such as benign prostatic hyperplasia, prostate inflammation, and rheumatoid arthritis (PCT/US2016/028720).

Ongoing and breakthrough pain is a primary concern for cancer patients. Over half of all cancer patients will experience severe, uncontrollable pain during the course of their diseases, and the management of pain is a primary challenge for cancer patients and the treating oncologists (List M A, Stracks J, Colangelo L, et al. *J. Clin. Oncol* (2000) 18: 877-884). Although cancer pain is a complex pathologic process and a formidable clinical problem, significant headway has been made in understanding the basic neurologic mechanisms that are responsible for generating cancer pain. The symptoms experienced by the cancer patient are a consequence of cellular, tissue, and systemic changes that occur during proliferation, invasion, and metastasis. The responding immune system also has a clear role in cancer pain. The cancer cell produces mediators that affect other cells within the cancer microenvironment, such as immune cells.

Cancer and immune cells in the region of tumor masses release several neuroimmune mediators that interact with a variety of receptors on peripheral nociceptive nerve terminals to promote abnormal discharge and hyperexcitability. In addition, tumors growing in the vicinity of peripheral nerves can compromise the integrity of the nerve, inducing a neuropathic condition accompanied by persistent pain, hyperalgesia, or allodynia. Both of these actions of tumors on peripheral nerve can result in central sensitization, which can further enhance the efficacy of nociceptive transmission through the spinal cord dorsal horn and perception of spontaneous and breakthrough pain (Hamamoto D T, Khasabov S G, Cain D M, Simone D A. *J. Neurophysiol* (2008) 100: 2300-2311, Sabino M A, Luger N M, Mach D B, Rogers S D, Schwei M J, Mantyh P W. *Int. J. Cancer* (2003) 104: 550-558).

Platinum drugs are rarely used as antiviral drugs. U.S. Pat. No. 8,247,445B2 reported the activity of a new platinum complex used in the prevention or treatment of virus and bacteria infections. U.S. Pat. No. 5,922,689 reported the use of cisplatin derivatives for the treatment of AIDS. Jiajiu Shaw et al. reported in patent literature (U.S. Pat. No. 6,297,245B1) that cisplatin was added with folic acid and coenzyme Q10 as a promoter to treat AIDS. Jiajiu Shaw et al. also disclosed that the new platinum drugs are used to treat and block new diseases caused by viruses, bacteria, and parasites, as well as to treat chronic and inflammatory diseases. Yang Xuqing et al. disclosed the use of dicycloplatin for antiviral or antibacterial purposes.

However, there remains a need for the drugs with good stability and high efficacy in the treatment and/or prevention of pain, inflammation, or diseases associated with viral infections.

SUMMARY OF THE INVENTION

In a first aspect, the present invention provides a combination product containing dicycloplatin and an acid. In some embodiments, the acid is selected from one or more of the following acids: 1,1-cyclobutanedicarboxylic acid, citric acid, chlorogenic acid, ferulic acid, maleic acid, salicylic acid, folic acid and gallic acid. In some embodiments, the ratio of dicycloplatin to the acids is 1:0.01 to 1:99. In some embodiments, the combination product optionally comprises one or more of the following additional components: coenzyme Q10, curcumin, glutathione, oryzanol, citric acid, vitamin C, and anthocyanins. In some embodiments, the combination product can be present in the form of a composition or pharmaceutical composition, or dicycloplatin, acids, or other ingredients of the combination product can be independently be present as separate formulations.

In a second aspect, the invention provides a combination product comprising dicycloplatin and one or more of the following additional components: coenzyme Q10, curcumin, glutathione, oryzanol, citric acid, Vitamin C and anthocyanins In a third aspect, the present invention provides a use of the combination product described hereinabove in the manufacture of a medicament, wherein the medicament is for use in the treatment and/or prevention of pain, inflammation and a disease associated with a viral infection. In some embodiments, the pain is selected from pains caused by cancer or a cause other than cancer (e.g., hepatitis B, hepatitis C, or rheumatoid arthritis), the inflammation is selected from inflammations caused by cancer or a non-cancer cause (e.g., rheumatoid arthritis), the disease associated with viral infection is selected from diseases associated with an infection with hepatitis B virus, hepatitis C virus, Ebola virus or human immunodeficiency virus.

In a fourth aspect, the present invention provides a method of treating and/or preventing pain, inflammation and a disease associated with a viral infection, which comprises using the combination product as described hereinabove for the patients in need thereof. In some embodiments, the pain is selected from pain caused by cancer or a cause other than cancer (e.g., hepatitis B, hepatitis C, or rheumatoid arthritis), and the inflammation is selected from inflammations caused by cancer or a non-cancer cause (e.g., rheumatoid arthritis), and the disease associated with viral infection is selected from the diseases associated an infection with hepatitis B virus, hepatitis C virus, Ebola virus or human immunodeficiency virus. In some embodiments, the dose of the dicycloplatin in the combination product is 0.01 to 10 mg/kg of the patient's body weight, preferably 0.01 to 5 mg/kg of the patient's body weight. In some embodiments, the combination product can be administered by the following route: orally, mouth taken, inhalation spray, sublingual, rectal, transdermal, vaginal mucosa, transmucosal, topical, nasal or enteral administration, injection, such as intramuscular injection, subcutaneous injection, intramedullary injection, and intrathecal, direct brain administration, in situ administration, subcutaneous, intraperitoneal, intravenous injection, intra-articular synovium, sternum, endo, intrahepatic, intralesional, crani Intraperitoneal, intraperitoneal, nasal, or intraocular injection or other means of drug delivery. In some embodiments, the combination product can be in the form of a composition or pharmaceutical composition, or the dicycloplatin, acid, or other ingredients of the combination product can independently be present as separate formulations, which can be administered simultaneously, continuously, or at intervals. The time interval includes, but not limited to, an integer value from 1 to 24 hours, such as 1 hour, 2 hours, or 3 hours; and an integer value from 1 to 30 days, such as 1 day, 2 days, or 3 days.

In a fifth aspect, the present invention provides a method of preparation of the combination product, which comprises 1) adding dicycloplatin as an active ingredient or as the sole active ingredient, and 2) optionally adding an acid to form a mixture, wherein the ratio of dicycloplatin to the acid is 1:0.01 to 1:99, preferably 1:3 to 1:10, and the acid is selected from one or more of the following: 1,1-cyclobutanedicarboxylic acid, citric acid, chlorogenic acid, ferulic acid, maleic acid, salicylic acid, folic acid and gallic acid, and 3) optionally adding one or more additional ingredients selected from the following: coenzyme Q10, curcumin, glutathione (GSH), oryzanol, citric acid, vitamin C and anthocyanins In the fifth aspect, the present invention further provides a method of preparation of a composition comprising dicycloplatin, or dicycloplatin and 1,1-cyclobutanedicarboxylic acid, the method comprising: 1) stirring carboplatin and 1,1-cyclobutanedicarboxylic acid at a molar ratio of 1:1.05 to 1:99, in a suitable solvent, at room temperature or under heat, for an appropriate period of time to obtain a mixture comprising dicycloplatin and 1,1-cyclobutanedicarboxylic acid; and optionally 2) lyophilizing the mixture directly, concentrating the mixture, adding a suitable amount of water to fully dissolve and then lyophilizing the mixture, or formulating the mixture into a desired aqueous solution, thereby obtaining the composition comprising dicycloplatin and 1,1-cyclobutanedicarboxylic acid.

In a sixth aspect, the present invention provides a use of dicycloplatin as the sole active ingredient in the manufacture of a medicament, wherein the medicament is for use in the treatment and/or prevention of pain or inflammation, wherein the pain is caused by cancer or another cause (such as by hepatitis B virus, hepatitis C virus, or rheumatoid arthritis), and the inflammation is an inflammation caused by cancer or a non-cancer cause (e.g., rheumatoid arthritis).

In a seventh aspect, the present invention provides a use of the combination product described hereinabove for treating and/or preventing pain, inflammation, and a disease associated with a viral infection.

In a eighth aspect, the present invention provides a composition comprising dicycloplatin as the sole active ingredient and a method of preparing such mixture, the method comprising adding dicycloplatin as thesole active ingredient.

In a ninth aspect, the present invention provides a use of dicycloplatin as the sole active ingredient in the manufacture of a medicament, wherein the medicament is for use in the treatment and/or prevention of pain or inflammation. In some embodiments, the pain is a pain caused by cancer or by a cause other than cancer, and the inflammation is an inflammation caused by cancer or by a cause other than cancer (e.g., rheumatoid arthritis).

In a tenth aspect, the present invention provides a composition containing dicycloplatin as the sole active ingredient for use in the treatment and/or prevention of pain or inflammation. In some embodiments, the pain is a pain caused by cancer, or pain caused by a cause other than cancer (e.g., hepatitis B, hepatitis C or rheumatoid arthritis), and the inflammation is caused by cancer or by a cause other than cancer (e.g., rheumatoid arthritis).

FIGURE AND DESCRIPTIONS

DEFINITION

Figure 1:
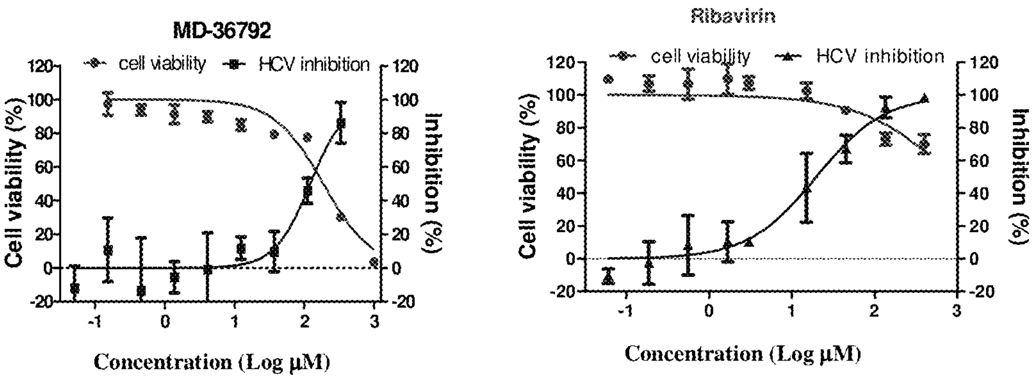
FIG. 1 shows the effect of Dicycloplatin or ribavirin alone on hepatitis C virus (HCV).

As used herein, the term "subject" is meant to include humans and animals, e.g., dogs, cats, rabbits, chickens, monkeys, etc.

As described herein, the term "dosage" refers to amount of the active ingredient used, e.g., milligrams (mg), to per kilogram (kg) of the subject's body weight.

As described herein, the term "ratio" generally refers to a molar ratio. For example, the mole ratio of dicycloplatin to the acid is 1:0.01 to 1:99. Content % of dicycloplatin, refers to weight percentage.

As described herein, the term "disease associated with a viral infection" refers to a disease caused by a viral infection or a disease accompanying a viral infection. The viral infection includes, but not limited to hepatitis virus (e.g., hepatitis A virus, hepatitis B virus, hepatitis C virus, etc.), Ebola virus, or human immunodeficiency virus infection.

As described herein, the term "pain" refers to the pain caused by a tumor (e.g., cancer), or pain caused by another cause (e.g., hepatitis B, hepatitis C, or rheumatoid arthritis).

As described herein, the terms "MD36792, AA011, and VK021" refer to dicycloplatin, glutathione, and vitamin C, respectively.

As described herein, the term "room temperature" means 25° C.±1° C. And, if the experimental temperature is not specified, it is referring to room temperature.

As described herein, the term "about" refers to ±10% of the value modified by the term, more preferably ±5%, and most preferably ±2%, so those skilled in this field should clearly defined the scope of the term "about" according to the value emblished.

DETAILED DESCRIPTION OF THE INVENTION

The inventors of the present application have found that the dicycloplatin claimed in the present application, as a main active ingredient, exhibits significant efficacy in the treatment and/or prevention of pain, especially in pain caused by cancer patients. Among cancer patients, especially patients with advanced liver cancer, kidney cancer, bone metastases, and bone cancer, the taken choice is to use dicycloplatin injection or oral compositions as the only treatment method. The inventors found that a certain number of patients with advanced cancer showed no sensitivity to dicycloplatin, with no observed efficacy on tumor suppression. However, dicycloplatin still showed obvious effect on cancer pain relief, and even caused the pain to disappear. Some patients used dicycloplatin for a certain course of treatment and then stopped treatment, these patients did not suffer pain again even after they stopped using dicycloplatin.

It has been found in the clinical treatment of tumor patients that dicycloplatin has a good effect on tumor-induced tissue edema and inflammation. In many cases, lung cancer patients with brain metastases took dicycloplatin orally or through injection. In these patients, it was found that after using dicycloplatin for one to two weeks, tissue edema in the brain caused by cancer metastasis was basically eliminated. This shows that dicycloplatin has a good anti-inflammatory effect. In many cases of liver cancer patients with hepatic tissue edema, after dicycloplatin infusion or oral administration for a period of time, the tissue edema significantly disappeared or reduced.

In a first aspect, the present invention provides a combination product, wherein the combination product comprises dicycloplatin and an acid, or consists of dicycloplatin and an acid. In some embodiments, the acid is selected from one or more of the following acids: 1,1-cyclobutanedicarboxylic acid, citric acid, chlorogenic acid, ferulic acid, maleic acid, salicylic acid, folic acid and gallic acid. In some embodiments, the ratio of the dicycloplatin to the acid is 1:0.01 to 1:99, preferably about 1:1, about 1:1.08, about 1:2, about 1:3, about 1:4, about 1:5, about 1:6, about 1:7, about 1:8, about 1:9, about 1:10, about 1:20, about 1:30, about 1:40, about 1:50, about 1:60, about 1:70, about 1:80, about 1:90, and a range of ratios among the ratios, including but not limited to about 1:1 to about 1:2, about 1.08 to about 1:2, about 1:3 to about 1:10, and so on. In some embodiments, the combination product optionally comprises one or more of the following additional components: coenzyme Q10, curcumin, glutathione, oryzanol, citric acid, vitamin C, and anthocyanins. In some embodiments, the ratio of dicycloplatin to the additional other components is about 0.1:1 to about 100:1, preferably about 0.1:1, about 0.2:1, about 0.3:1, about 0.4:1, about 0.43:1, about 0.5:1, about 0.6:1, about 0.7:1, about 0.8:1, about 0.9:1, about 1:1, about 1:1.25, about 1.02:1, about 2:1, about 3:1, about 4:1, about 5:1, about 6:1, about 7:1, about 8:1, about 9:1, about 10:1, about 20:1, about 30:1, about 40:1, about 50:1, about 60:1, about 70:1, about 80:1, about 90:1, and the range of ratios among the ratios, including but not limited to about 0.1:1 to 10:1, about 0.4:1 to about 8:1, about 0.43:1 to about 5:1, about 0.43:1 to about 1:1.25, about 0.43:1 to about 1:1.02, and the like. Preferably, the ratio of dicycloplatin to the described additional other components (coenzyme Q10, vurcumin, glutathione, oryzanol, citric Acid, vitamin C and anthocyanins) is: about 0.1:1 to 10:1, about 0.4:1 to about 8:1, about 0.43:1 to about 5:1, about 0.43:1 to about 1:1.25, about 0.43:1 to about 1:1.02. More preferably, the ratio of dicycloplatin to vitamin C is about 0.43:1, the ratio of dicycloplatin to glutathione is about 1:1.25, the ratio of dicycloplatin to coenzyme Q10 is about 1.02:1. Further, the weight percentage of the dicycloplatin in the compositions is about 5%, about 10%, about 15%, about 16.64%, about 18.29%, about 19.11%, about 19.87%, about 20%, about 20%, about 25%, approximately 30%, approximately 35%, approximately 40%, approximately 44.46%, approximately 45%, approximately 50%, approximately 55%, approximately 60%, approximately 60.5%, approximately 65%, approximately 70%, approximately 75%, about 80%, about 85%, about 90%, about 95%, about 96.2%, about 99%, and ranges between the respective percentages, including but not limited to about 5% to 99%, 16.64% to 60.5%, about 18.29% to 44.46%, and about 19.11% to about 35%.

In some embodiments, the combination product can be present in the form of a composition or pharmaceutical composition, or the dicycloplatin, acid, or other ingredients of the combination product can be independently be present as separate formulations. In some embodiments, the combination product can be oral formulations, such as capsules, tablets, granules, a lyophilized formulation or aqueous injection, a nebulizer formulation, or other formulations.

In a second aspect, the invention provides a combination product comprising dicycloplatin and one or more of the following additional components: coenzyme Q10, curcumin, glutathione, oryzanol, citrate, vitamin C and anthocyanins In some embodiments, the comination product optionally comprises acid(s), selected from one or more of the following: 1,1-cyclobutanedicarboxylic acid, citric acid, chlorogenic acid, ferulic acid, maleic acid, salicylic acid, folic acid and gallic acid. In some embodiments, the ratio of dicycloplatin to the acid is: 1:0.01 to 1:99, preferably about 1:1, about 1:1.08, about 1:2, about 1:3, and about 1:4, about 1:5, about 1:6, about 1:7, about 1:8, about 1:9, about 1:10, about 1:20, about 1:30, about 1:40, about 1:50, about 1:60, about 1:70, about 1:80, about 1:90, and a range of ratios among the ratios, including but not limited to about 1:1 to about 1:2, about 1.08 to about 1:2, about 1:3 to about 1:10, and so on. In some embodiments, ratio of dicycloplatin to the further other components is about 0.1:1 to about 100:1, preferably about 0.1:1, about 0.2:1, about 0.3:1, about 0.4:1 about 0.43:1, about 0.5:1, about 0.6:1, about 0.7:1, about 0.8:1, about 0.9:1, about 1:1, about 1:1.25, about 1.02:1, about 2:1, about 3:1, about 4:1, about 5:1, about 6:1, about 7:1, about 8:1, about 9:1, about 10:1, about 20:1, about 30:1 about 40:1, about 50:1, about 60:1, about 70:1, about 80:1, about 90:1, and the range of ratios among the ratios, including but not limited to about 0.1:1 to 10:1, about 0.4:1 to about 8:1, about 0.43:1 to about 5:1, about 0.43:1 to about 1:1.25, about 0.43:1 to about 1:1.02, and the like. Preferably, the ratio of dicycloplatin to the described additional other components (coenzyme Q10, curcumin, glutathione, oryzanol, citric acid, vitamin C and anthocyanins) is: about 0.1:1 to 10:1, about 0.4:1 to about 8:1, about 0.43:1 to about 5:1, about 0.43:1 to about 1:1.25, and about 0.43:1 to about 1:1.02. More preferably, the ratio of dicycloplatin to vitamin C is about 0.43:1, the ratio of dicycloplatin to glutathione is about 1:1.25, the ratio of dicycloplatin to coenzyme Q10 is about 1.02:1. Further, the weight percentage of dicycloplatin in the compositions is about 5%, about 10%, about 15%, about 16.64%, about 18.29%, about 19.11%, about 19.87%, about 20%, about 20% by weight. 25%, approximately 30%, approximately 35%, approximately 40%, approximately 44.46%, approximately 45%, approximately 50%, approximately 55%, approximately 60%, approximately 60.5%, approximately 65%, approximately 70%, approximately 75%, about 80%, about 85%, about 90%, about 95%, about 96.2%, about 99%, and ranges between the respective percentages, including but not limited to about 5% to 99%, 16.64% to 60.5%, About 18.29% to 44.46%, and about 19.11% to about 35%.

In some embodiments, the combination product can be oral formulations, such as capsules, tablets, granules, a lyophilized formulation or aqueous injection, a nebulizer formulation, or other formulations.

In a third aspect, the present invention provides a use of dicycloplatin, such as the combination product described hereinabove, in the manufacture of a medicament, wherein the medicament is for use in the treatment and/or prevention of pain, inflammation and a disease associated with a viral infection. In some embodiments, the pain is selected from pains caused by cancer or a cause other than cancer (e.g., hepatitis B, hepatitis C, or rheumatoid arthritis), the inflammation is selected from inflammations caused by cancer or a non-cancer cause (e.g., rheumatoid arthritis), the disease associated with viral infection is selected from diseases associated with an infection with hepatitis B virus, hepatitis C virus, Ebola virus or human immunodeficiency virus.

In a fourth aspect, the present invention provides a method of treating and/or preventing pain, inflammation and a disease associated with a viral infection, which comprises administering dicycloplatin such as the combination product as described hereinabove to the patients in need thereof. In some embodiments, the pain is selected from pain caused by cancer or a cause other than cancer (e.g., hepatitis B, hepatitis C, or rheumatoid arthritis), and the inflammation is selected from inflammations caused by cancer or a non-cancer cause (e.g., rheumatoid arthritis), and the disease associated with viral infection is selected from the diseases associated an infection with hepatitis B virus, hepatitis C virus, Ebola virus or human immunodeficiency virus. In some embodiments, the dose of the dicycloplatin in the combination product is 0.01 to 10 mg/kg of the patient's body weight, preferably 0.01 to 5 mg/kg of the patient's body weight. In some embodiments, the combination product can be administered by the following route: orally, mouth taken, inhalation spray, sublingual, rectal, transdermal, vaginal mucosa, transmucosal, topical, nasal or enteral administration, injection, such as intramuscular injection, subcutaneous injection, intramedullary injection, and intrathecal, direct brain administration, in situ administration, subcutaneous, intraperitoneal, intravenous injection, intra-articular synovium, sternum, endo, intrahepatic, intralesional, crani Intraperitoneal, intraperitoneal, nasal, or intraocular injection or other means of drug delivery. In some embodiments, the combination product can be in the form of a composition or pharmaceutical composition, or the dicycloplatin, acid, or other ingredients of the combination product can independently be present as separate formulations, which can be administered simultaneously, continuously, or at intervals. The time interval includes, but not limited to, an integer value from 1 to 24 hours, such as 1 hour, 2 hours, or 3 hours; and an integer value from 1 to 30 days, such as 1 day, 2 days, or 3 days.

In a fifth aspect, the present invention provides a method of preparation of the combination product, which comprises 1) adding dicycloplatin as an active ingredient or as the sole active ingredient, and 2) optionally adding an acid to form a mixture, wherein the ratio of dicycloplatin to the acid is 1:0.01 to 1:99, preferably about 1:1, about 1:1.08, about 1:2, about 1:3, about 1:4, about 1:5, about 1:6, about 1:7, about 1:8, about 1:9, about 1:10, about 1:20, about 1:30, about 1:40, about 1:50, about 1:60, about 1:70, about 1:80, about 1:90, and a range of ratios among the ratios include but not limited to about 1:1 to about 1:2, about 1.08 to about 1:2, about 1:3 to about 1:10, and the acids are selected from one or more of the following as 1,1-cyclobutanedicarboxylic acid, citric acid, chlorogenic acid, ferulic acid, maleic acid, salicylic acid, folic acid and gallic acid; and 3) optionally adding one or more additional ingredients selected from the following: coenzyme Q10, curcumin, glutathione (GSH), oryzanol, citric acid, vitamin C and anthocyanins, wherein the ratio of dicycloplatin to the additional other components is about 0.1:1 to about 100:1, preferably about 0.1:1, about 0.2:1, about 0.3:1, about 0.4:1, about 0.43:1, about 0.5:1, about 0.6:1, about 0.7:1, about 0.8:1, about 0.9:1, about 1:1, about 1:1.25, about 1.02:1, about 2:1, about 3:1, about 4:1, about 5:1, about 6:1, about 7:1, about 8:1, about 9:1, about 10:1, about 20:1, about 30:1, about 40:1, about 50:1, about 60:1, about 70:1, about 80:1, about 90:1, and the range of ratios among the ratios includes but not limited to about 0.1:1 to 10:1, about 0.4:1 to about 8:1, about 0.43:1 to about 5:1, about 0.43:1 to about 1:1.25, about 0.43:1 to about 1:1.02, etc.; preferably, the ratio of dicycloplatin to the other components (coenzyme Q10, curcumin, glutathione, oryzanol, citric acid, vitamin C and anthocyanins) is: about 0.1:1 to 10:1, about 0.4:1 to about 8:1, about 0.43:1 to about 5:1, about 0.43:1 to about 1:1.25, about 0.43:1 to about 1:1.02; more preferably, the ration of dicycloplatin to vitamin C turns to be about 0.43:1, the ratio of dicycloplatin to glutathione is about 1:1.25, the ratio of dicycloplatin to coenzyme Q10 is about 1.02:1.

As described herein, aqueous solution containing dicycloplatin and 1,1-cyclobutanedicarboxylic acid (with ration ranging from 1:1.2 to 1:20) is stable at 40° C. for seven weeks. The aqueous solution of dicycloplatin with gallic acid, salicylic acid, citric acid, ferulic acid, etc. is stable at 40° C., but dicycloplatin begins to decompose after two weeks. Preferably, the above-mentioned acid is 1,1-cyclobutanedicarboxylic acid, and preferably, the ratio of dicycloplatin to 1,1-cyclobutanedicarboxylic acid is 1:1.2 to 1:20.

In some embodiments, the present invention provides a method of preparation of a composition comprising dicycloplatin or dicycloplatin and 1,1-cyclobutanedicarboxylic acid, the method comprising: 1) stirring carboplatin and 1,1-cyclobutanedicarboxylic acid at a molar ratio of 1:1.05 to 1:99 (such as, 1:1.2, 1:1.5, 1:3, 1:5, 1:10, 1:20 and any ratio among the ratios, including but not limited to 1:1.2 to 1:20, or the ratio can be selected according to the actual needs, e.g. in the proportion described herein above), in a suitable solvent (preferably water), at room temperature or under heat (preferably 40° C.), for an appropriate period of time, such as 0.5 to 24 hours (preferably 0.5 hour, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, or any range between them), to obtain a mixture comprising dicycloplatin and 1,1-cyclobutanedicarboxylic acid; and optionally 2) lyophilizing the mixture directly, concentrating the mixture, adding a suitable amount of water to fully dissolve and then lyophilizing the mixture, or formulating the mixture into a desired aqueous solution, thereby obtaining the composition comprising dicycloplatin and 1,1-cyclobutanedicarboxylic acid. Compared with the methods reported previously, the present invention has many advantages, such as easier operation process, higher yield of dicycloplatin, and complete consumption of carboplatin. Moreover, the resulting lyophilized mixture was composed of dicycloplatinum and 1,1-cyclobutanedicarboxylic acid, and no carboplatin residue was detected.

In a sixth aspect, the present invention provides a use of dicycloplatin as an active ingredient or the sole active ingredient in the manufacture of a medicament, wherein the medicament is for use in the treatment and/or prevention of pain or inflammation, wherein the pain is caused by cancer or another cause (such as by hepatitis B virus, hepatitis C virus, or rheumatoid arthritis), and the inflammation is an inflammation caused by cancer or a non-cancer cause (e.g., rheumatoid arthritis).

In a seventh aspect, the present invention provides combination product containing dicycloplatin and an acid or consisting of dicycloplatin and an acid, for treating and/or preventing pain caused by cancer or a cause other than cancer, e.g., hepatitis B, hepatitis C or rheumatoid arthritis, inflammation caused by cancer or another non-cancer cause, e.g., rheumatoid arthritis, and a disease associated with a viral infection, wherein the disease associated with the viral infection are selected from a disease associated with an infection with hepatitis B virus, hepatitis C virus, Ebola virus or human immunodeficiency virus. In some emobodiments, the acid is selected from one or more of the following: 1,1-cyclobutanedicarboxylic acid, citric acid, chlorogenic acid, ferulic acid, maleic acid, salicylic acid, folic acid and gallic acid. In somebodments, the composition comprises one or more of the following other additional components: coenzyme Q10, curcumin, glutathione, oryzanol, citric acid, vitamin C, and anthocyanins.

As an alternative, the combination product contains dicycloplatin and one or more of the following additional components: coenzyme Q10, curcumin, glutathione, oryzanol, citric acid, vitamin C, and anthocyanins. In some embodiments, the compositions optionally contain an acid selected from one or more of the following: 1,1-cyclobutanedicarboxylic acid, citric acid, chlorogenic acid, ferulic acid, maleic acid, salicylic acid, folic acid and gallic acid.

In some embodiments, the ratio of the dicycloplatin to the acid is about 1:0.01 to about 1:99, preferably about 1:1, about 1:1.08, about 1:2, about 1:3, about 1:4, about 1:5, about 1:6, about 1:7, about 1:8, about 1:9, about 1:10, about 1:20, about 1:30, about 1:40, about 1:50, about 1:60, about 1:70, about 1:80, about 1:90, and a range of ratios among the ratios, including but not limited to about 1:1 to about 1:2, about 1.08 to about 1:2, about 1:3 to about 1:10, and so on. In some embodiments, the ratio of the dicycloplatin to the further other components is about 0.1:1 to about 100:1, preferably about 0.1:1, about 0.2:1, about 0.3:1, about 0.4:1, about 0.43:1, about 0.5:1, about 0.6:1, about 0.7:1, about 0.8:1, about 0.9:1, about 1:1, about 1:1.25, about 1.02:1, about 2:1, about 3:1, about 4:1, about 5:1, about 6:1, about 7:1, about 8:1, about 9:1, about 10:1, about 20:1, about 30:1, about 40:1, about 50:1, about 60:1, about 70:1, about 80:1, about 90:1, and the range of ratios between the respective ratios, including but not limited to about 0.1:1 to 10:1, about 0.4:1 to about 8:1, about 0.43:1 to about 5:1, about 0.43:1 to about 1:1.25, about 0.43:1 to about 1:1.02 and so on. Preferably, the ratio of dicycloplatin to the described additional other components (folate, coenzyme Q10, curcumin, glutathione, oryzanol, citric acid, gallic acid, vitamin C, and anthocyanins) is: about 0.1:1 to about 10:1, about 0.4:1 to about 8:1, about 0.43:1 to about 5:1, about 0.43:1 to about 1:1.25, and about 0.43:1 to about 1:1.02. More preferably, the ratio of dicycloplatin to vitamin C is about 0.43:1, the ratio of dicycloplatin to glutathione is about 1:1.25, the ratio of dicycloplatin to coenzyme Q10 is about 1.02:1. In some embodiments, the combination product can be present in the form of a composition or pharmaceutical composition, or the dicycloplatin, acid, or other ingredients of the combination product can be independently present as separate formulations.

In a eighth aspect, the present invention provides a composition comprising dicycloplatin as the sole active ingredient, wherein the composition comprises an excipient slected from the following: magnesium stearate, hydroxypropyl cellulose, pregelatinized starch, chitosan, β-cyclodextrin, and polyvinylpyrrolidone, and a method of preparing such mixture, wherein the method comprisies adding dicycloplatin as the sole active ingredient with optional excipient described hereinabove.

In a ninth aspect, the present invention provides a use of dicycloplatin as an active ingredient or the sole active ingredient in the manufacture of a medicament, wherein the medicament is for use in the treatment and/or prevention of pain or inflammation. In some embodiments, the pain is a pain caused by cancer or pain caused by a cause other than cancer (e.g., hepatitis B, hepatitis C, or rheumatoid arthritis), and the inflammation is an inflammation caused by cancer or inflammation caused by a cause other than cancer (e.g., rheumatoid arthritis).

In a tenth aspect, the present invention provides a composition containing dicycloplatin as an active ingredient or the sole active ingredient for use in the treatment and/or prevention of pain or inflammation. In some embodiments, the pain is a pain caused by cancer, or pain caused by a cause other than cancer (e.g., hepatitis B, hepatitis C or rheumatoid arthritis), and the inflammation is caused by cancer or by a cause other than cancer (e.g., rheumatoid arthritis).

In other aspects, the invention provides a method to treat and/or prevent pain, the method comprising administering an effective dose of dicycloplatin to a patient in need thereof. In some embodiments, the patient is a cancer patient, preferably a patient suffering from liver cancer, kidney cancer, bone metastasis, brain metastasis or bone cancer, more preferably advanced cancer patient, or a patient who has already developed resistance to a platinum based anticancer drugs, most preferably a patient with advanced liver cancer. Further, the effective dose of the dicycloplatin may be lower than the effective anticancer dose of dicycloplatin in the cancer patient, or in some embodiments, the effective dose of dicycloplatin can be equal to the effective anticancer dose used in the cancer patient. For example, dicycloplatin can be used as the only drug to treat cancer and pain. In some embodiments, the dicycloplatin can be used as the sole active substance for treating and/or preventing pain. In some embodiments, the treatment method further comprises using one or more other active substances having analgesic effects. In some embodiments, the method further comprises using one or more active substances having an anticancer effect, wherein the active substance having an anticancer effect is preferably a non-platinum based anticancer drugs. In some embodiments, dicycloplatin is present in the form of a pharmaceutical composition. Further, the dicycloplatin is contained in the combination product as defined herein above.

In other aspects of the invention, the effective dose of dicycloplatin to treat and/or prevent pain may be lower than the effective anticancer dose, and the dicycloplatin has an analgesic effect in cancer patients who are already resistant to platinum drugs' antitumor activity. Therefore, methods or uses of dicycloplatin in the treatment and/or prevention of pain are not limited to cancer patients, and dicycloplatin has shown a significant analgesic effect comparable to the positive control drug rotunidin in the pain animal model experiments shown herein. As shown herein, dicycloplatin can have analgesic effects on pain caused by cancer or a non-cancer cause, including but not limited to hepatitis B, hepatitis C, and rheumatoid arthritis. In some embodiments, in the method and use hereinabove for treating and/or preventing pain, the patient in need thereof is not a cancer patient. In some embodiments, in the method and use hereinabove for treating and/or preventing pain, the patient in need thereof is a cancer patient who has developed resistance to a platinum-based anticancer drug.

In other aspects, the present invention provides a method to treat and/or prevent tissue edema (e.g., liver edema, brain edema, etc.) or inflammation, the method comprising administering an effective dose of dicycloplatin to a patient in need thereof. In some embodiments, the patient is a cancer patient, preferably a patient with liver cancer, kidney cancer, bone metastasis, brain metastasis or bone cancer, more preferably a patient with advanced cancer, most preferably a patient with advanced liver cancer or a patient who has developed resistance to a platinum based anticancer drug. In some embodiments, the effective dose of dicycloplatin can be lower than the effective anticancer dose of dicycloplatin in the cancer patient, or in some embodiments, the effective dose of dicycloplatin can be equal to the effective anticancer dose used in the cancer patient. In some embodiments, the method further includes using one or more active substances having anticancer effects on the patient, wherein the active substances having anticancer effects are preferably a non-platinum anticancer drug. In some embodiments, the patient is not a cancer patient. In some embodiments, the dicycloplatin is present in the form of a pharmaceutical composition. Further, the dicycloplatin is contained in the combination product as defined hereinabove.

In other aspects, the invention provides a method to treat and/or prevent diseases associated with a viral infection, such as a method to reduce viral index, the method comprising administering an effective dose of a pharmaceutical composition to a patient in need thereof, wherein the pharmaceutical composition comprises dicycloplatin and glutathione. In some embodiments, the viral infection is an infection with a hepatitis B virus, a hepatitis C virus, an Ebola virus, and/or a human immunodeficiency virus infection. In some embodimetns, the viral infection is an infection with a hepatitis B virus. In some embodimetns, the viral infection is an infection with a hepatitis C virus. In some embodimetns, the viral infection is an infection with an Ebola virus. In some embodimetns, the viral infection is an infection with a human immunodeficiency virus. In some embodiments, the method comprises administering an effective dose of the pharmaceutical compositions to the patients with 1-3 times a day. In some embodiments, the method comprising administering to the patient an effective dose of the pharmaceutical composition for at least 7 days, preferably, for from 1 month to 1 year, for example, 1, 2, 3, 4, 5, 6, 7, 8, 9, 10, 11, 12 months, preferably, for 1 to 6 months, for example, 1, 2, 3, 4, 5, 6 months. In some embodiments, the patient is not treated with any other antiviral drug treatment, and/or has not received any other antiviral drug treatment. In some embodiments, the method also includes administering other antiviral drugs to the patient. In some embodiment, the pharmaceutical composition optionally comprises one or more of the following additional other components: coenzyme Q10, curcumin, oryzanol, citric acid, vitamin C, and anthocyanins. Preferably, the ratio of dicycloplatin to glutathione is about 0.1:1 to about 100:1, preferably about 0.1:1, about 0.2:1, about 0.3:1, about 0.4:1, about 0.43:1, about 0.5:1, about 0.6:1, about 0.7:1, about 0.8:1, about 0.9:1, about 1:1, about 1:1.25, about 1.02:1, about 2:1, about 3:1, about 4:1, about 5:1, about 6:1, about 7:1, about 8:1, about 9:1, about 10:1, about 20:1, about 30:1, about 40:1, about 50:1, about 60:1, about 70:1, about 80:1, about 90:1, and the range of ratios among the ratios, including but not limited to about 0.1:1 to 10:1, about 0.4:1 to about 8:1, about 0.43:1 to about 5:1, about 0.43:1 to about 1:1.25, about 0.43:1 to about 1:1.02, and the like. The ratio of dicycloplatin to glutathione is about 0.1:1 to 10:1, about 0.4:1 to about 8:1, about 0.43:1 to about 5:1, about 0.43:1 to about 1:1.25, about 0.43:1 to about 1:1.02. More preferably, the ratio of dicycloplatin to glutathione is about 1:1.25. Preferably, dicycloplatin and glutathione are present in the same pharmaceutical composition when treating diseases associated with viral infections. However, in some embodiments, dicycloplatin and glutathione can be independently present as separate formulations, which may be administered simultaneously, continuously, or at regular intervals.

In some embodiments, in the method hereinabove for treating and/or preventing pain, inflammation, and diseases related to viral infections, dicycloplatin or the pharmaceutical compositions may be present in the form of: oral formulations, such as capsules, tablets, granules, or frozen dry formulations, or water injections, or nebulizers, or other formulations. In some embodiment, in the method hereinabove for treating and/or preventing pain, inflammation, and diseases related to viral infection, the dicycloplatin or the pharmaceutical composition can be administered by: oral taken, mouth, inhalation spray, sublingual, rectal, transdermal, vaginal mucosa, transmucosal, topical administration, nasal or intestinal administration, injection administration, such as intramuscular, subcutaneous, intramedullary, and intrathecal, direct brain administration, orthotopic administration, subcutaneous, intraperitoneal, intravenous, intraarticular synovial, sternum, intrahepatic, intralesional, intracranial, intraperitoneal, nasal, or intraocular injection or other drug delivery methods. Preferably, the dicycloplatin or pharmaceutical composition can be administered orally or by injection.

DETAILED DESCRIPTION

The invention is further described below with reference to the drawings and specific embodiments. It should be understood that the following examples are only used to illustrate the present invention and are not used to limit the scope covered by the claims of the present invention.

Dicycloplatin mentioned in the examples could be purchased commercially or prepared by the methods described herein. Other compounds or the acids and other components described herein are well known to the public in the fields, can be purchased commercially or obtained through known synthetic methods.

DETECTION METHODS

The detection methods used in the examples in this article are as follows:

(1) X-ray Powder Diffraction (XRPD)

Analytical Instrument: Panalytical Empyrean.

The X-ray powder diffraction was conducted by mounting a sample of the crystalline material on a Si single crystal low-background holder and spreading out the sample into a thin layer with the aid of a microscope slide. The 2θ position was calibrated against Panalytical 640 Si powder standard. The sample irradiated with X-rays generated by a copper long-fine focus tube operated at 45 kV and 40 mA with a wavelength of Kα1=1.540589 angstroms and Kα2=1.544426 angstroms (Kα1/Kα2 intensity ratio is 0.50). The collimated X-ray source was passed through a programmed divergence slit set at 10 mm and the reflected radiation directed through a 5.5 mm anti-scatter slit. The sample was exposed for 16.3 seconds per 0.013° 2-theta increment (continuous scan mode) over the range 3 degrees to 40 degrees 2-theta in theta-theta mode. The running time was 3 minutes and 57 seconds. The instrument was equipped with a RTMS detector (X'Celerator). Control and data capture was by means of a Dell Optiplex 780 XP operating with data collector software.

As is known the relative intensity of peaks can be affected by the following factors, for example, grains above 30 microns in size and non-unitary aspect ratios that may affect analysis of samples. In addition, the position of reflections can be affected by the precise height at which the sample sits in the diffractometer and the zero calibration of the diffractometer. The surface planarity of the sample may also have a small effect. Hence the diffraction pattern data presented are not to be taken as absolute values.

(2) Differential Scanning Calorimetry (DSC)

As a thermal analysis method, DSC is used to measure the amount of heat required to warm up the samples, and the reference value as a function of temperature is also measured. The general procedure for measuring DSC is known. The specific instruments and conditions used in the described examples are as follows:

Analytical Instrument: TA Instruments Q2000 DSC.

Heating rate: 10° C. per minute.

Purge gas: nitrogen

Thermal Gravimetric Analysis (TGA)

TGA is used to measure the change in physical and chemical properties of a sample as a function of elevated temperature, usually at a constant heating rate, or as a function of time (with constant temperature and/or constant mass loss). The general procedure for measuring TGA is known. The specific instruments and conditions used in the described examples are as follows:

Analytical Instrument: TA Instruments Q5000 TGA.

Heating rate: 10° C. per minute.

Purge gas: nitrogen.

Example 1

Preparation of Dicycloplatin Compositions 1) 5.0 g of carboplatin (13.47 mmol) and 2.232 g of 1,1-cyclobutanedicarboxylic acid (15.50 mmol) were added to a 20 mL glass flask.

2) 15 mL of deionized water was added to the above glass vial and stirred at room temperature to form a uniform suspension while keeping the vial away from the light source.

3) Cooling to 20° C., the obtained mixture was transferred to a 500 mL reaction flask, and rinse with 50 mL deionized water.

4) Another 175 mL of deionized water was added and well stirred and kept at 20° C. for 2 hours to form a uniform solution.

5) The mixture was filtered. The filtrate was lyophilized and dried under vacuum.

6) 7.21 g of mixture of dicycloplatin and 1,1-cyclobutanedicarboxylic acid was obtained.

7) It was measured that dicycloplatin weighed 96.20%. DCP/1,1-cyclobutanedicarboxylic acid ratio is 1:0.15.

The product was analyzed by XRPD, DSC and $^1$H NMR as described above.

Example 2

Preparation of Dicycloplatin Compositions 1) 5.0 g of carboplatin (13.47 mmol) and 22.32 g of 1,1-cyclobutanedicarboxylic acid (155.0 mmol) were added to a 200 mL glass flask 2) 125 mL of deionized water was added to the above glass vial and stirred at room temperature to form a uniform suspension while keeping the vial away from the light source.

3) Cooling to 20° C., the obtained mixture was transferred to a 500 mL reaction flask, and rinse with 150 mL deionized water.

4) Another 2000 mL of deionized water was added and well stirred and kept at 20° C. for 2 hours to form a uniform solution.

5) The mixture was filtered. The filtrate was lyophilized and dried under vacuum.

6) 72.1 g of mixture of dicycloplatin and 1,1-cyclobutanedicarboxylic acid was obtained.

7) It was measured that dicycloplatin weighed 96.22%. DCP/1,1-cyclobutanedicarboxylic acid ratio is 1:10.15.

The product was analyzed by XRPD, DSC and $^1$H NMR as described above.

Example 3

Preparation of Combination Product Containing 1,1-Cyclobutanedicarboxylic Acid, Citric Acid and Dicycloplatin 1) 5.0 g of carboplatin (13.47 mmol) and 3. 879g of 1,1-cyclobutanedicarboxylic acid (26. 94 mmol) were added to a 50 mL glass flask.

2) 25 mL of deionized water was added to the above glass vial and stirred at room temperature to form a uniform suspension while keeping the vial away from the light source.

3) Cooling to 20° C., the obtained mixture was transferred to a 500 mL reaction flask, and rinse with 50 mL deionized water.

4) Another 225 mL of deionized water was added and well stirred and kept at 20° C. for 2 hours to form a uniform solution.

5) 2.588 g (13.47 mmol) of citric acid was added to the above solution, and kept stirred to form a homogeneous solution.

6) The mixture was filtered. The filtrate was lyophilized and dried under vacuum.

7) 11.462 g of mixture of dicycloplatin and 1,1-cyclobutanedicarboxylic acid was obtained.

8) It was measured that dicycloplatin weighed 60.50%. DCP/1,1-cyclobutanedicarboxylic acid/citric acid ratio:1:1:1.

The product was analyzed by XRPD, DSC and $^1$H NMR as described above.

Example 4

Preparation of Combination Product Containing 1,1-Cyclobutanedicarboxylic Acid, Citric Acid, GSH and Dicycloplatin 1) 5.0 g of carboplatin (13.47 mmol) and 3.879 g of 1,1-cyclobutanedicarboxylic acid (26. 94 mmol) were added to a 50 mL glass flask.

2) 25 mL of deionized water was added to the above glass vial and stirred at room temperature to form a uniform suspension while keeping the vial away from the light source.

3) Cooling to 20° C., the obtained mixture was transferred to a 500 mL reaction flask, and rinse with 50 mL deionized water.

4) Another 225 mL of deionized water was added and well stirred and kept at 20° C. for 2 hours to form a uniform solution.

5) 2.588 g (13.47 mmol) of citric acid, and 4.135 g of glutathione (GSH, 13.47 mmol) were added to the above solution, and kept stirred to form a homogeneous solution.

6) The mixture was filtered. The filtrate was lyophilized and dried under vacuum.

7) 15.60 g of mixture of dicycloplatin, glutathione and 1,1-cyclobutanedicarboxylic acid was obtained.

8) It was measured that dicycloplatin weighed 44.46%. DCP/1,1-cyclobutanedicarboxylic acid/citric acid/GSH ratio:1:1:1:1.

The product was analyzed by XRPD, DSC and $^1$H NMR as described above.

Example 5

Preparation of Combination Product Containing 1,1-cyclobutanedicarboxylic Acid, Chlorogenic Acid, Glutathione, Vitamin C and Dicycloplatin 1) 5.15 g of dicycloplatin (13.47 mmol), 2.232 g of 1,1-cyclobutanedicarboxylic acid (15.50 mmol), 4.77 g of chlorogenic acid (13.47 mmol), 4.135 g of glutathione (GSH, 13.47 mmol)), 11.862g of vitamin C were mixed well.

2) Then 28.15 g of dicycloplatin-containing combination product was obtained.

7) Dicycloplatin content was measured up to weighed 18.29%.

The product was analyzed by XRPD, DSC and $^1$H NMR as described above.

Example 6

Preparation of a Combination Product Containing Chlorogenic Acid, Glutathione, Vitamin C and Dicycloplatin 1) 5.15 g of dicycloplatin (13.47 mmol), 4.77 g of chlorogenic acid (13.47 mmol), 4.135 g of glutathione (GSH, 13.47 mmol), and 11.862 g of vitamin C were thoroughly mixed.

2) 25.92 g dicycloplatin combination products was obtained.

7) Dicycloplatin content was determined to be 19.87%.

The product was analyzed by XRPD, DSC and $^1$H NMR as described above.

Example 7

Preparation of Combination Product Containing Glutathione, Vitamin C and Dicycloplatin 1) 5.15 g of dicycloplatin (13.47 mmol), 4.135 g of glutathione (GSH, 13.47 mmol), and 11.862 g of vitamin C was thoroughly mixed.

2) 21.147 g of dicycloplatin-containing combination product was obtained.

7) Dicycloplatin weight was determined to be 24.35%.

The product was analyzed by XRPD, DSC and 1H NMR as described above.

Example 8

Preparation of a Combination Product Containing Folic Acid, Chlorogenic Acid, Glutathione, Vitamin C and Dicycloplatin 1) 5.15 g of dicycloplatin (13.47 mmol), 1.03 g of folic acid, 4.77 g of chlorogenic acid (13.47 mmol), 4.135 g of glutathione (GSH, 13.47 mmol), and 11.862 g of vitamin C were thoroughly mixed.

2) 26.95 g of dicycloplatin-containing combination product was obtained.

7) Dicycloplatin weight was determined to be 19.11%.

The product was analyzed by XRPD, DSC and $^1$H NMR as described above.

Example 9

Preparation of a Combination Product Containing Coenzyme Q10, Chlorogenic Acid, Glutathione, Vitamin C and Dicycloplatin 1) 5.15 g of dicycloplatin (13.47 mmol), 5.03 g of coenzyme Q10, 4.77 g of chlorogenic acid (13.47 mmol), 4.135 g of glutathione (GSH, 13.47 mmol), and 11.862 g of vitamin C were mixed thoroughly.

2) 30.95 g of dicycloplatin-containing combination product was obtained.

7) Dicycloplatin weight was determined to be 16.64%.

The product was analyzed by XRPD, DSC and $^1$H NMR as described above.

Example 10

Preparation of a Combination Product Containing Coenzyme Q10, Citric Acid, Chlorogenic Acid, Flutathione, Vitamin C and Dicycloplatin 1) 5.15 g of dicycloplatin (13.47 mmol), 5.03 g of coenzyme Q10, 4.77 g of citric acid, 4.135 g of glutathione (GSH, 13.47 mmol), and 11.862 g of vitamin C were mixed thoroughly.

2) 30.95 g of dicycloplatin-containing combination product was obtained.

7) Dicycloplatin weight was determined to be 16.64%.

The product was analyzed by XRPD, DSC and $^1$H NMR as described above.

Example 11

Preparation of a Combination Product Containing Oryzanol, Citric Acid, Glutathione, Vitamin C and Dicycloplatin 1) 5.15 g of bicyclic platinum (13.47 mmol), 5.03 g of oryzanol, 4.77 g of citric acid, 4.135 g of glutathione (GSH, 13.47 mmol), and 11.862 g of vitamin C were mixed thoroughly.

2) 30.95 g of dicycloplatin-containing combination product was obtained.

7) Dicycloplatin weight was determined to be 16.64%.

The product was analyzed by XRPD, DSC and $^1$H NMR as described above.

Example 12

Study on the In Vitro Activity of MD36792 (Dicycloplatin) on Hepatitis C Virus (HCV)

(I) Experimental Materials

1. Compounds: MD36792 (Dicycloplatin) and Ribavirin (commercially available).
2. Cell: Huh7.5.1 cells.
3. Virus: Hepatitis C virus (HCV type 2a, JFH1-Luc virus strain).
4. Experimental reagents: DMEM medium, alamarBlue® kit (Invitrogen), Luciferase Assay System kit (Promega) and other experimental reagents.

(II) Experimental Methods

1. Cytotoxicity Test of MD36792

Experimental principle: The experiment uses alamarBlue® (Invitrogen) kit to detect the toxic effect of drugs on cells. alamarBlue® is a redox indicator that produces changes in absorbance and fluorescent signals based on cellular metabolic activity. alamarBlue® is easily soluble in water. After its oxidized form enters cells, it is followed by reduction by mitochondrial enzymes to produce measurable fluorescence and color changes. It is used for quantitative analysis of cell viability and cell proliferation, and for in vitro cytotoxicity studies. This assay is based on the ability of cells with metabolic activity to convert reagents into fluorescent and colorimetric indicators. Damaged and inactive cells have lower natural metabolic activity and lower corresponding signals, so the strength of fluorescence signal can reflect the level of cell activity.

Method steps: Huh7.5.1 cells were seeded in a 96-well cell culture plate, and the cells were attached after use. DMSO was used to continuously dilute the drug from a 200-fold initial concentration to a 3-fold gradient into 6 gradients, and then DMEM complete medium was used to dilute the drug-containing culture solution, and each well was tested in duplicate. After 72 hours of incubation, the culture supernatant was discarded, and the medium containing alamarBlue® was added. After incubation at 37° C. for 4 hours, fluorescence readings were detected at 570 nm and 595 nm.

cell viability (%)=(sample well-blank control)/(cell control-blank control)*100% Calculation formula 2. MD36792 Experiment Against Hepatitis C Virus (HCV)

Experimental principle: After the HCV strain JFH1-Luc containing the Rluc reporter gene infected Huh7.5.1 cells, Rluc was expressed as the virus replicated, and the expression level of the Rluc reporter gene could reflect the HCV virus replication level. Experimental steps: (1) Cell plating: Huh7.5.1 cells were seeded in 96-well cell culture plates, and the cells were adhered to the wall for later use. (2) Viral infection: The drug is serially diluted from 2 times as the initial concentration and 3 times as the gradient to 9 gradients in the culture medium. Each concentration has 2 repeating wells. 100 μL of the drug-containing culture solution is added to the cell wells, and then infected with JFH1-luc virus culture medium 100 μL. (3) Detection: cultured for 72 hours after virus infection, Rluc readings were detected using the Renilla Luciferase Assay Kit.

In the experiment, Ribavirin-positive drug control group, virus control group and cell control group were set.

inhibition rate (%)=100%−(drug group-cell control group)/(virus control group-cell control group) *100% Calculation formula Experimental results: As shown in FIG. 1, MD36792 has an $EC_{50}$ (50% inhibition) of HCV of 121.1 μM, so the selection index SI ($SI=CC_{50}/EC_{50}$) of MD36792 is 1.54. Since the replication of HCV in this model requires high cell status, when the drug has a cytotoxic effect, it will seriously affect the replication of the virus. Therefore, we believe that the inhibitory effect of 333 μM and 111 μM on HCV is caused by toxic effects. Therefore, MD36792 has no inhibitory effect on HCV. The control drug Ribavirin has a significant inhibitory effect on HCV.

Example 13

Study on the In Vitro Activity of MD36792 (Dicycloplatin) on Hepatitis B Virus (HBV)

(I) Experimental Materials

1. Compound: MD36792.
2. Cell: HepAD38 cells.
3. Virus: Hepatitis B virus (HBV).
4. Experimental reagents: DMEM/F12 medium, CellTiter-Glo detection kit (Promega), HBeAg antigen detection kit (Kehua), HBsAg antigen detection kit (Kehua), and other experimental reagents.

(II) Experimental Methods

1. Cytotoxicity Test of MD36792

Experimental principle: CellTiter-Glo kit (Promega) was used to detect the toxic effect of drugs on cells. The CellTiter-Glo kit detects the number of living cells in the culture by quantifying ATP. The respiration of metabolically active cells and other life activities can produce ATP. The stable glow type produced by luciferase is used in the kit Signaling, while luciferase requires ATP in the process of light emission. An equal volume of CellTiter-Glo reagent was added to the cell culture medium and for measuring the luminescence value. The light signal is proportional to the amount of ATP in the system, and ATP is positively related to the number of living cells. Therefore, the light signal value can reflect the number of living cells.

Method steps: HepAD38 cells were seeded in a 96-well cell culture plate, and the cells were adhered to the wall for later use. The drug was serially diluted from 1 mM to 9 gradients in 9 gradients with 2 replicates per gradient. The drug was added to the cells and cultured in a $CO_2$ incubator at 37° C. After 3 days of drug addition and culture, the cytopathic effect (CPE) caused by the drug was observed under a light microscope, and CellTiter-Glo was added to detect the cell survival rate. The toxicity of a drug to cells is expressed as the activity of the cells.

cell activity (%)=(drug group-blank control)/(cell control-blank control)*100%  Calculation formula 2. MD36792 Experiment Against Hepatitis B Virus (HBV)

Experimental principle: The replication of HBV in HepAD38 cell line can be regulated by tetracycline. After the dox is removed, the integrated HBV genome can be transcribed to form pgRNA, and pgRNA continues to be reverse transcribed into rc DNA. The synthesized rc DNA will re-enter the nucleus to form cccDNA. HBeAg can be expressed only from cccDNA, and the expression of HBeAg can reflect the synthesis amount of cccDNA. Therefore, we use ELISA to detect the content of HBeAg and detect the inhibitory effect of drugs on HBV. In this cell, HBsAg can be continuously transcribed and translated from integrated HBV DNA. We also tested the HBsAg content to determine the effect of the drug on HBV replication.

Figure 2:
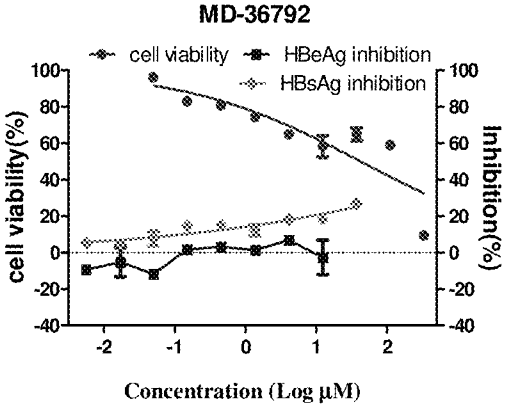
FIG. 2 shows the effect of Dicycloplatin on hepatitis B virus (HBV).

Experimental steps: (1) Cell plating: HepAD38 cells with Dox removed for 3 days were seeded in 96-well plates and cultured in a $CO_2$ incubator at 37° C. for 24 hours. (2) Dosing treatment: Dilute MD36792 with DMEM/F12 complete medium (10% FBS) from 333 μM, dilute 9 gradients in 3 times in a row, and 2 duplicate wells per gradient. The diluted drug was added to the cells and cultured in a $CO_2$ incubator at 37° C. for 72 hours. (3) Detection: Take the supernatant and use the HBeAg antigen detection kit and HBsAg antigen detection kit to detect the expression of HBeAg and HBsAg, respectively.

antigen inhibition rate (%)=100%−(drug group-blank control)/(cell control group-blank control)*100%  Calculation formula Experimental results: As shown in FIG. 2, MD36792 had no inhibitory effect on the expression of HBeAg (e antigen) and HBsAg (surface antigen) of HBV.

Example 14

Study on the In Vitro Activity of MD36792 (Dicycloplatin) Against Human Immunodeficiency Virus (HIV)

(I) Experimental Materials

1. Compounds: MD36792 and Zidovudine (AZT) (commercially available).
2. Cell: MT4 cells.
3. Virus: Human Immunodeficiency Virus (HIV).
4. Experimental reagents: RPMI-1640 medium, CellTiter-Glo detection kit (Promega) and other experimental reagents.

(II) Experimental Methods

1. MD36792 Cytotoxicity Test

Experimental principle: CellTiter-Glo kit (Promega) was used to detect the toxic effect of drugs on cells. The CellTiter-Glo kit detects the number of living cells in the culture by quantifying ATP. The respiration of metabolically active cells and other life activities can produce ATP. The stable glow type produced by luciferase is used in the kit Signaling, while luciferase requires ATP in the process of light emission. An equal volume of CellTiter-Glo reagent was added to the cell culture medium for measuring the luminescence value. The light signal is proportional to the amount of ATP in the system, and ATP is positively related to the number of living cells. Therefore, the light signal value can reflect the number of living cells.

Method steps: MT4 cells were seeded in a 96-well cell culture plate, and the cells were adhered to the wall for later use. The drug was serially diluted from 1 mM to 9 gradients in 9 gradients with 2 replicates per gradient. The drug was added to the cells and cultured in a $CO_2$ incubator at 37° C. The cytopathic effect (CPE) caused by the drug was observed under a light microscope, and CellTiter-Glo was added to detect the cell survival rate. The toxicity of a drug to cells is expressed as the activity of the cells.

cell activity (%)=(drug group-blank control)/(cell control-blank control)*100  Calculation formula 2. MD36792 Experiments Against Human Immunodeficiency Virus (HIV)

Experimental principle: MT-4 cell protection experiments were used to detect compounds against viruses.

Experimental steps: A 3-fold diluted drug was added to a 96-well plate, which incubates the LAI virus and MT-4 cells and inoculates it into the well plate. After culture, when the virus infects the control wells, a significant CPE appears. Reagent CellTiter-Glo was added and mixed, then the chemiluminescence signal is to be detected.

The experiment set the cell control (uninfected cell control), virus control, and positive drug control (Zidovudine, AZT).

Inhibition rate (%)=(drug group-virus control)/(cell control-virus control)*100%

Figure 3:
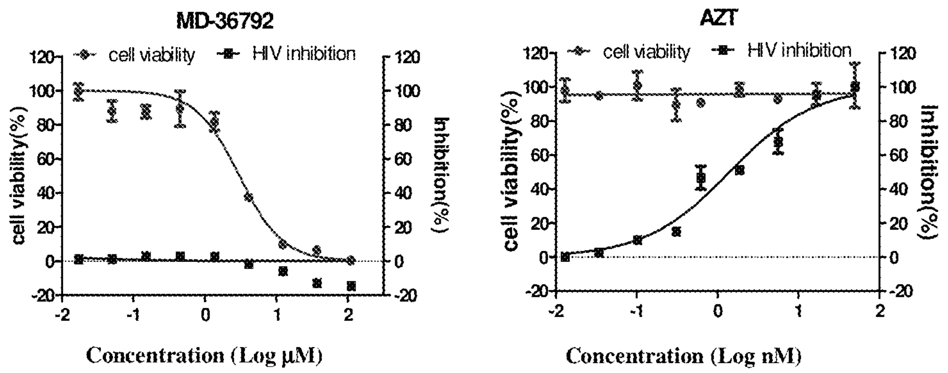
FIG. 3 shows the effect of Dicycloplatin or zidovudine on HIV.

Experimental results: As shown in FIG. 3, MD36792 has no inhibitory effect on HIV infection, while the control drug zidovudine has a significant inhibitory effect on HIV.

Example 15

Study on the In Vitro Activity of MD36792 (Bicyclic Platinum) Anti-Ebola Virus (I) Experimental Materials 1. Compound: MD36792.
2. Cells: MDCK cells.
3. Virus: Ebola virus.
4. Experimental reagents: DMEM medium, alamarBlue® kit (Invitrogen), Luciferase Assay System kit (Promega) and other experimental reagents.

(II) Experimental Methods

1. MD36792 Cytotoxicity Test

Experimental principle: The experiment uses alamarBlue® (Invitrogen) kit to detect the toxic effect of drugs on cells. alamarBlue® is a redox indicator that produces changes in absorbance and fluorescent signals based on cellular metabolic activity. alamarBlue® is easily soluble in water. After its oxidized form enters cells, it is followed by reduction by mitochondrial enzymes to produce measurable fluorescence and color changes. It is used for quantitative analysis of cell viability and cell proliferation, and for in vitro cytotoxicity studies. This assay is based on the ability of cells with metabolic activity to convert reagents into fluorescent and colorimetric indicators. Damaged and inactive cells have lower natural metabolic activity and lower corresponding signals, so the strength of fluorescence signal can reflect the level of cell activity.

Experimental procedure: MDCK cells were seeded in a 96-well cell culture plate, and the cells were adhered to a stand-by. The drug was serially diluted from 1 mM to 9 gradients in 9 gradients with 2 replicates per gradient. The drug was added to the cells and cultured in a $CO_2$ incubator at 37° C. After 2 days of dosing and incubation, observation on the cytopathic effect (CPE) caused by the drug was taken under a light microscope. Then alamarBlue® medium was added, and incubated at 37° C. for 4 h, then the fluorescence readings was detected at 570 nm and 595 nm. The toxicity of a drug to cells is expressed as the activity of the cells.

cell activity (%)=(drug group-blank control)/(cell control-blank control)*100% Calculation formula 2. MD36792 Anti-Ebola Virus Experiment Experimental principle: After Ebola virus containing Rluc reporter gene infects cells, Rluc is expressed as the virus replicates. The expression level of Rluc reporter gene can reflect the level of adenovirus infection.

Method steps: (1) Cell plating: MDCK cells were seeded in a 96-well cell culture plate, and the cells were used after adherence. (2) Dosing treatment: Dilute the drug 3 times successively into 9 drug concentration groups with maintenance medium (2% FBS), and configure it into 2× drug-containing culture solution with 2 replicates per gradient. After the cells have grown into a monolayer, 100 μl of 2× drug-containing DMEM culture medium was added, then followed by 100 μl of DMEM diluted Ebola virus, and incubated at 37° C. (3) Detection: After culture for 48 hours after virus infection, Rluc readings were detected using Luciferase Assay Kit.

Figure 4:
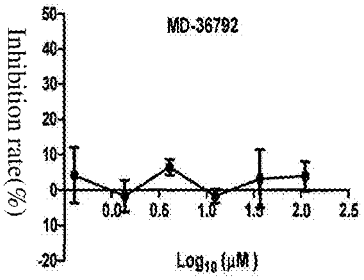
FIG. 4 shows the effect of Dicycloplatin on Ebola virus.

The virus control group and the cell control group were set in the experiment.

inhibition rate (%)=100%−(drug group-cell control group)/(virus control group-cell control group) *100% Calculation formula Experimental results: As shown in FIG. 4, MD36792 has no inhibitory effect on Ebola virus infection.

Example 16

A Study of the In Vivo Activity of Dicycloplatin Alone (Orally or by Injection) on Patients with Hepatitis B, Hepatitis C, HIV Infection and Ebola Virus Infection The aqueous dicycloplatin injection injection was purchased from Beijing Xingda Technology System Co., Ltd. and the specification was 50 mg/5 mL. Dicycloplatin used in oral preparations is prepared with reference to US2016/0297842, which is obtained by dissolving dicycloplatin in deionized water.

Experimental methods: (1) Twelve HBV patients were given dicycloplatin alone for 1-3 months, and the virus index and liver function were observed. Six of them were administered by intravenous drip, and 150 mg of dicycloplatinum aqueous solution was dissolved in 250 ml of 5% dextrose aqueous solution once every two days; 6 of them were administered orally, and 150 mg of aqueous dicycloplatin solution was dissolved in 250 ml of 5% dextrose aqueous solution. Once every two days. (2) Dicycloplatin was given to 9 patients with hepatitis C separately for 1-3 months. Observation of viral index and liver function was performed by intravenous drip. 150 mg of aqueous dicycloplatin solution was dissolved in 250 ml of 5% glucose aqueous solution. It was taken once every two days; 6 of them were taken orally, and 150 mg of aqueous dicycloplatin solution was dissolved in 250 ml of a 5% glucose aqueous solution. It was taken once every two days;. (3) Dicycloplatin was given to 8 HIV-infected individuals alone (viral index>>100000 IU/mL) for 1-3 months (oral and injection in four patients) to observe the viral index and liver function; dicycloplatin (reference to the above method, intravenous glucose aqueous solution) was given separately to 20 Ebola virus infected people (Africa) for 1-3 weeks, and the virus index and liver function were observed.

Experimental results: (1) Dicycloplatin was given to 12 hepatitis B patients alone for 1-3 months. None of the patients showed a downward trend in the virus index, while the virus index continued to rise, and liver function did not improve; Dicycloplatin alone was given to 9 patients with hepatitis C for 1-3 months. None of the patients showed a downward trend in the virus index, while the virus index continued to rise, and liver function did not improve; (3) 8 dicycloplatin alone was given to 8 HIV infected patients (Virus Index>>100000 IU/mL). After 1-3 months of use (oral and injection in four patients), none showed a downward trend in the patient's viral index, while the viral index continued to increase, and liver function did not improve; Dicycloplatin was given alone to 20 Ebola-infected patients (Africa) for 1-3 weeks. None of the patients showed a downward trend in the virus index, and while the virus index continued to rise, without any control or remission.

Example 17

Study on the In Vivo Activity of Combination Products Containing Dicycloplatin on Patients with Hepatitis B, Hepatitis C, and HIV Infection.

Experimental methods: (1) The combination product was used in 15 patients with hepatitis B (without taking any other antiviral drugs), and after 1-3 months of treatment, the viral index and liver function index were observed; 6 of them were tested by taking capsules containing combination products prepared by experiment 4, which the capsule can be prepared according to the conventional technology known to those skilled in the art. Referring to the amount of dicycloplatin, it was once taken every two days with 150 mg of the dosage of dicycloplatin; 9 cases took the combined product prepared by Experiment 10. Referring to the amount of dicycloplatin, it was taken once every two days in a dose of 150 mg dicycloplatin capsules; (2) The combined product was used in 13 patients with hepatitis C (without any antiviral treatment). After 1-3 months of treatment, the observation was taken on virus index and liver function indicators; 5 of them took the combination product prepared in Experiment 7. Referring to the amount of dicycloplatin, it was taken three times a day in the dose of 50 mg dicycloplatin of capsules; 8 of them used the combination product prepared by Experiment 11. Referring to the amount of dicycloplatin, it was taken three times a day, in a dose of 50 mg dicycloplatin capsules; (3) The combined product was used in 8 HIV-infected patients (without taking any other antiviral drugs), observation was taken on the virus index and liver function indicators; 2 of them used the combination product prepared by Experiment 4, three times a day. Referring to the amount of dicycloplatin, the dose is 50 mg capsules; 6 of them used the combined product prepared by Experiment 11. Referring to the amount of dicycloplatin, they used three times a day in a dose of 50 mg of dicycloplatin capsuled.

Experimental results: It was disclosed in the present invention that the combined products containing dicycloplatin was used in 15 patients with hepatitis B (without taking any other antiviral drugs). After 1-3 months of treatment, the virus index decreased significantly and liver function are basically normal; the combined product containing dicycloplatin was used in 13 patients with hepatitis C (without taking any other antiviral drugs). After 1-3 months of treatment, the virus index decreased significantly. In 2 cases, the virus index dropped below the detection limit, and the liver function index was basically normal. The combination product containing dicycloplatin disclosed in the present invention was used in 8 patients with HIV infection (without taking any other antiviral drugs). During treatment, the virus index decreased significantly, the $CD_4$ index increased significantly, and liver function indicators were basically normal.

Example 18

Study on the In Vivo Activity of Combination Product Containing Dicycloplatin on Patients with Hepatitis C and HIV Infection The following cases (1) and (2) used the capsuled combination product prepared by Experiment 6, where the capsules can be prepared according to conventional techniques known to those skilled in the art. 150 mg of dicycloplatin of capsules was taken per day; the following cases (3), (4) used the capsuled combination product prepared by Experiment 10, where the capsules can be prepared according to conventional techniques known to those skilled in the art. Referring to dicycloplatin dosage, the dosage of 150 mg capsules was taken per day.

Experimental methods: (1) Hepatitis C patient Mr. He, 61 years old, was not reactive with anti-interferon and other antiviral drugs. The RNA virus index continued to rise. The RNA virus index quantified 472,000 IU/mL. He suffered typical liver pain. One month after oral administration of the combination product containing dicycloplatin, the patient received the detection of the RNA virus index and liver function indicators; (2) Hepatitis C patient Mr. Wang, 51 years old, without taking any treatment, belongs to hepatitis C type III, whose RNA virus index quantified was 932,000 IU/mL, and his liver showed typical pain and pressure. After taking the combination product containing dicycloplatin for one month, the patient received observation of his liver pain and pressure. Then after another two months, the RNA virus index and liver function index was checked; (3) A female patient, 43 years old, received the virology test and was confirmed to be HIV positive and clinical type C2. The test results showed that the $CD_4$ lymphocyte count was 312, $CD_4$ cells were 319, and $CD_4/CD_8$=0.58: 1. Four months after oral administration of the combination product containing dicycloplatin, $CD_4$, $CD_8$ cells and their ratios were detected; (4) A female patient, 28 years old, received the virological test and was confirmed to be HIV positive, 190 of $CD_4$ cells, 815 of $CD_8$ cells, and $CD_4/CD_8$=0.23 1. Six months after oral administration of the combination product containing dicycloplatin, $CD_4$, $CD_8$ cells and their ratios were detected.

Experimental results: (1) Hepatitis C patient, Mr. He, 61 years old, took a combination of product containing dicycloplatin for one month, and the quantitative RNA virus index decreased from 472000 IU/mL to 4,520 IU/mL. The main indicators of liver function did not change significantly, and the patient's pain disappeared; (2) Hepatitis C patient, Mr. Wang, 51 years old, after taking a combination product containing dicycloplatin for one month, the pain and pressure disappeared, and continued to take it for two months. His RNA virus index quantification decreased to below 1000 IU/mL, and liver function is basically normal; (3) The female patient of 43 years old above, is indeed HIV positive by the virological test, clinical type C2. The test results showed $CD_4$ Lymphocyte count was 312, $CD_4$ cells were 319, and $CD_4/CD_8$=0.58:1. Four months after oral administration of a combination product containing dicycloplatin, the test results showed the following as: $CD_4$ cells were 568, $CD_8$ was 606, and $CD_4/D_8$=0.92:1. (4) The female patient of 28 years old, was HIV positive by virological examination, and her $CD_4$ cells were 190, her $CD_8$ was 815, and $CD_4/CD_8$=0.23:1. After six months of oral administration of a combination product containing dicycloplatin, no virological test were detectable, with $CD_4$ of 563, $CD_8$ of 575, and $CD_4/CD_8$=0.97:1.The above results show that dicycloplatin has a low direct antiviral activity. The results of using dicycloplatin or a dicycloplatin combination product alone from patients infected with multiple viruses show that dicycloplatin alone does not show clinical efficacy in antiviral treatment in patients. The combination product of dicycloplatin is used to treat people infected with HCV, HBV and HIV, and the effect is remarkable.

Example 19

Study on the Stability of Combination Products Containing Dicycloplatin

The invention disclosed combination preparation by mixing dicycloplatin with various acids. In order to achieve more stability of dicycloplatin and try to improve its solubility, the present invention disclosed the ratio of dicycloplatin and various acids to form a mixture and the preparation methods thereof.

(1) Method to obtain a mixture of dicycloplatin and 1,1-cyclobutanedicarboxylic acid Using the conventional preparation method, the mixtures may be obtained by mixing dicycloplatin and a certain proportion of 1,1-cyclobutanedicarboxylic acid, otherwise by lyophilization of aqueous mixture of dicycloplatin and a certain proportion of 1,1-cyclobutanedicarboxylic acid, which both completely dissolved in water. XRPD characterization and $^1$H-NMR showed no change of the stability of dicycloplatin after mixing.

The combination mixtures may be prepared from carboplatin and a certain proportion of 1,1-cyclobutanedicarboxylic acid in water as a medium. The mixtures undertake being stirred at 0-40° C. for 1 to 24 hours, then directly lyophilized and mixed uniformly to give the desired mixtures. Or the mixtures may be obtained from direct lyophilization of the clear solution prepared by adding appropriate amount of water to the above mixtures. XRPD structure and $^1$-NMR showed that the mixture was composed of dicycloplatin and 1,1-cyclobutanedicarboxylic acid. No carboplatin residue was detected. This preparation method greatly improves the yield of dicycloplatin, and makes the raw materials of carboplatin consumed completely.

(2) Preparation of a mixture of dicycloplatin and citric acid, chlorogenic acid, citric acid, gallic acid, etc.

The combination products may be prepared by the conventional methods. It may be prepared by mixing dicycloplatin and a certain proportion of one or more of acids from 1,1-cyclobutanedicarboxylic acid, citric acid, chlorogenic acid, citric acid, gallic acid, ferulic acid, maleic acid, salicylic acid, etc.. Or it may be preprared by thoroughly dissolving dicycloplatin and a certain proportion of one or more acids in water and followed lyophilization, wherein acids are from 1,1-cyclobutane-dicarboxylic acid, citric acid, chlorogenic acid, citric acid, gallic acid, ferulic acid, and maleic acid, salicylic acid, etc. XRPD characterization and $^1$-NMR showed no change of the stability of dicycloplatin after mixing.

(3) Preparation of dicycloplatin or combination products thereof with other components.

Additional other components include coenzyme Q10, curcumin, glutathione (GSH), oryzanol, vitamin C and anthocyanins As shown in Examples 5-10, preparation of combination products using dicycloplatin as the main active ingredient can be performed by either conventional methods or a specific preparation method for a specific situation.

In many examples, dicycloplatinum is prepared as a lyophilized powder and water injection using water as a carrier. Stability experiments show that the formulation retains good stability. In many examples, dicycloplatinum has good compatibility and stability with corresponding pharmaceutical excipients, and thus is prepared into corresponding oral preparations.

Example 20

Study on the Stability of Dicycloplatinum with 1,1-cyclobutanedicarboxylic Acid and Excipients The stability of dicycloplatin contained combination product for eight consecutive weeks is shown in Table 1-4 below.

1. The solid product and solution product formed by dicycloplatin and 1,1-cyclobutanedicarboxylic acid (1:1.2 to 1:20 of dicycloplatin to the acid) are stable at 40° C. The above-mentioned solid product was examined for eight consecutive weeks under light conditions, and the results showed that it was stable.

TABLE 1

Study on the stability of dicycloplatin with 1,1-cyclobutanedicarboxylic acid and excipients

| Compositions state | Compositions state and ratio | start DCP (%) | After 1 day DCP (%) | After 3 days DCP (%) | After 5 days DCP (%) | After 2 wks DCP (%) | After 3 wks DCP (%) | After 4 wks DCP (%) | After 5 wks DCP (%) | After 6 wks DCP (%) | After 7 wks DCP (%) | After 8 wks DCP (%) | Note |
|---|---|---|---|---|---|---|---|---|---|---|---|---|---|
| Solid (40° C.) | Solid (1:1.2) | 92 | 91 | 94 | 94 | 96 | 93 | 90 | 91 | 91 | 94 | 92 | Stable |
| | Solid (1:1.5) | 86 | 86 | 85 | 82 | 86 | 84 | 84 | 83 | 87 | 89 | 88 | Stable |
| | Solid (1:3) | 65 | 62 | 62 | 66 | 65 | 67 | 47 | 59 | 61 | 63 | 64 | Stable |
| | Solid (1:5) | 40 | 38 | 42 | 45 | 44 | 43 | 39 | 40 | 39 | 40 | 42 | Stable |
| | Solid (1:10) | 28 | 30 | 27 | 27 | 30 | 29 | 26 | 28 | 29 | 28 | 29 | Stable |
| | Solid (1:20) | 15 | 15 | 16 | 16 | 16 | 16 | 15 | 15 | 15 | 16 | 16 | Stable |
| Aqueous solution (40° C.) | Aqueous solution (1:1.2) | 92 | 90 | 91 | 93 | 93 | 90 | 88 | 88 | 90 | 89 | 90 | Stable |
| | Aqueous solution (1:1.5) | 86 | 85 | 85 | 87 | 87 | 83 | 82 | 83 | 85 | 84 | 85 | Stable |
| | Aqueous solutio (1:3) | 65 | 63 | 61 | 62 | 62 | 58 | 58 | 59 | 62 | 61 | 63 | Stable |
| | Aqueous solution (1:5) | 40 | 39 | 39 | 40 | 40 | 37 | 37 | 38 | 39 | 39 | 39 | Stable |
| | Aqueous solution (1:10) | 28 | 30 | 29 | 30 | 30 | 28 | 28 | 28 | 29 | 29 | 29 | Stable |

TABLE 1-continued

Study on the stability of dicycloplatin with 1,1-cyclobutanedicarboxylic acid and excipients

| Compositions state | Compositions state and ratio | start DCP (%) | After 1 day DCP (%) | After 3 days DCP (%) | After 5 days DCP (%) | After 2 wks DCP (%) | After 3 wks DCP (%) | After 4 wks DCP (%) | After 5 wks DCP (%) | After 6 wks DCP (%) | After 7 wks DCP (%) | After 8 wks DCP (%) | Note |
|---|---|---|---|---|---|---|---|---|---|---|---|---|---|
| | Aqueous solution (1:20) | 15 | 16 | 16 | 16 | 16 | 15 | 15 | 15 | 15 | 17 | 16 | Stable |
| Solid Under light | Solid (1:1.2) | 92 | 94 | 93 | 94 | 95 | 91 | 90 | 93 | 92 | 92 | 93 | Stable |
| | Solid (1:1.5) | 86 | 86 | 89 | 86 | 84 | 83 | 85 | 86 | 88 | 85 | 88 | Stable |
| | Solid (1:3) | 65 | 68 | 67 | 64 | 66 | 63 | 61 | 60 | 58 | 62 | 63 | Stable |
| | Solid (1:5) | 40 | 44 | 45 | 40 | 43 | 42 | 40 | 41 | 41 | 42 | 43 | Stable |
| | Solid (1:10) | 28 | 29 | 30 | 28 | 30 | 29 | 27 | 28 | 31 | 29 | 29 | Stable |
| | Solid (1:20) | 15 | 15 | 16 | 16 | 16 | 15 | 15 | 15 | 16 | 15 | 15 | Stable |

2. The solid product formed by dicycloplatin and the acids, such as vitamin C, gallic acid, salicylic acid, citric acid, ferulic acid, etc., is stable at 40° C.

TABLE 2

Stability of the solid copositions formed by dicycloplatin and the acids, such as vitamin C, gallic cid, salicylic acid, citric acid, ferulic acid

| Compositions state | Compositions state and ratio | Start DCP (%) | After 1 day DCP (%) | After 3 days DCP (%) | After 5 days DCP (%) | After 2 wks DCP (%) | After 3 wks DCP (%) | After 4 wks DCP (%) | After 5 wks DCP (%) | Afte 6 wks DCP (%) | After 7 wks DCP (%) | After 8 wks DCP (%) | Note |
|---|---|---|---|---|---|---|---|---|---|---|---|---|---|
| Solid (40° C.) | DCP + VC (1:2) | 98 | 97 | 95 | 100 | 101 | 100 | 99 | 96 | 99 | 99 | 100 | Stable |
| | DCP + gallic acid (1:2) | 96 | 99 | 94 | 95 | 98 | 98 | 99 | 95 | 97 | 99 | 97 | Stable |
| | DCP + salicyclic acid (1:2) | 97 | 95 | 96 | 95 | 96 | 97 | 95 | 98 | 96 | 97 | 99 | Stable |
| | DCP + citric acid (1:2) | 97 | 98 | 93 | 95 | 96 | 99 | 93 | 95 | 97 | 96 | 97 | Stable |
| | DCP + ferulic acid (1:2) | 98 | 100 | 96 | 99 | 99 | 100 | 98 | 96 | 95 | 98 | 97 | Stable |

3. The solution product formed by dicycloplatin and gallic acid, salicylic acid, citric acid, ferulic acid, etc., begins to decompose at 40° C. basically after two weeks.

TABLE 3

Stability of aqueous solution product formed by dicycloplatin and gallic acid, salicylic acid, citric acid, ferulic acid,

| Composition state | Compositions and ratio | Start DCP (%) | After 1 day DCP (%) | After 3 days DCP (%) | After 5 days DCP (%) | After 2 wks DCP (%) | After 3 wks DCP (%) | After 4 wks DCP (%) | After 5 wks DCP (%) | After 6 wks DCP (%) | Afte 7 wks DCP (%) | After 8 wks DCP (%) | Note |
|---|---|---|---|---|---|---|---|---|---|---|---|---|---|
| Aqueous solution (40° C.) | DCP + VC (1:2) | 98 | 90 | 84 | 84 | 70 | 61 | 58 | 58 | 57 | 57 | 56 | Decomposed after 2 days |
| | DCP + Gallic | 96 | 94 | 96 | 97 | 92 | 81 | 76 | 72 | 70 | 63 | 58 | Decomposed after 2 |

TABLE 3-continued

| Stability of aqueous solution product formed by dicycloplatin and gallic acid, salicylic acid, citric acid, ferulic acid, | | | | | | | | | | | | | |
|---|---|---|---|---|---|---|---|---|---|---|---|---|---|
| Composition state | Compositions and ratio | Start DCP (%) | After 1 day DCP (%) | After 3 days DCP (%) | After 5 days DCP (%) | After 2 wks DCP (%) | After 3 wks DCP (%) | After 4 wks DCP (%) | After 5 wks DCP (%) | After 6 wks DCP (%) | Afte 7 wks DCP (%) | After 8 wks DCP (%) | Note |
| | acid (1:2) | | | | | | | | | | | | weeks |
| | DCP + Salicylic acid (1:2) | 94 | 93 | 94 | 96 | 95 | 89 | 89 | 90 | 90 | / | / | Decomposed after 3 weeks |
| | DCP + Citric Acid (1:2) | 97 | 94 | 90 | 92 | 91 | 84 | 86 | 85 | 87 | 88 | 87 | Decomposed after 2 days |
| | DCP + Ferulic acid (1:2) | 98 | / | / | / | / | / | / | / | / | / | / | Decomosed after 1 day |

4. The stability experiments of dicycloplatin mixing with the corresponding excipients prove that mixtures with single or multiple excipients are stable for 8 consecutive weeks at 40° C.

TABLE 4

| Stability experiments of dicycloplatin mixing with the corresponding excipients | | | | | | | |
|---|---|---|---|---|---|---|---|
| time/DCP (%) dose | MD36792 + talcum powder 1 g + 1 g | | MD36792 + Micro powder silicone 1 g + 0.5 g | | MD36792 + Magnesium stearate 1 g + 0.5 g | | Note |
| conditions | 40° C. | illumination | 40° C. | illumination | 40° C. | illumination | Stable |
| start | 101 | 101 | 101 | 101 | 101 | 101 | Stable |
| After 1 day | 102 | 103 | 101 | 99 | 103 | 102 | Stable |
| After 3 days | 100 | 103 | 101 | 100 | 102 | 100 | Stable |
| After 5 days | 103 | 102 | 100 | 97 | 102 | 103 | Stable |
| After 10 days | 102 | 99 | 99 | 98 | 101 | 102 | Stable |
| After 15 days | 103 | 99 | 99 | 99 | 101 | 103 | Stable |
| After 20 dasy | 103 | 102 | 100 | 100 | 103 | 103 | Stable |
| After 30 days | 102 | 101 | 101 | 100 | 102 | 102 | Stable |

Notes:
1. MD36792 refers to dicycloplatin;
2. The ratio refers to the molar ratio of dicycloplatin (DCP) to 1,1-cyclobutanedicarboxylic acid;
3. High temperature experimental conditions are T = 40° C.;
4. The lighting experiment conditions are 2000LX;
5. Solution concentration: 1 mg/ml;
6. The error is within range of 2% up and down.

Example 21

Effect of Dicycloplatin on Pain and Inflammation

The inventors of the present application have discovered that dicycloplatin, as the main active ingredient, shows a significant effect in the treatment of pain caused by cancer patients. Among cancer patients, it is suitable especially to patients with advanced liver cancer, kidney cancer, bone metastases, brain metastases and bone cancer. The patients may take the treatment of using dicycloplatin injection or oral preparations as the only treatment method, as shown Table 5. The inventors also found that a certain number of patients with advanced cancer showed no sensitivity to dicycloplatin and no effect on tumor suppression. However, the obvious relief effect of dicycloplatin on cancer pain is still obvious, and even the pain disappears. Some patients stopped using dicycloplatin after a certain course of dicycloplatin treatment, and no pain occurred again.

TABLE 5

Effect of dicycloplatin on pain as the main active ingredient

| cases | $5^{th}$ day | $17^{th}$ day | $31^{st}$ day, then stop taking | $60^{th}$-$90^{th}$ (without using DCP ) | Effect on tumor supressiong |
|---|---|---|---|---|---|
| Lung cancer to bone metastasis 5 cases | Pain gone | No pain | No pain | No pain | No obvious change after 4 weeks of treatment |
| Bone cancer 3 cases | Pain gone | No pain | No pain | No pain | No obvious change after 4 weeks of treatment |
| Liver cancer 5 cases | Pain gone | No pain | No pain | No pain | No obvious change after 4 weeks of treatment |
| Lung cancer to brain metastasis 2 cases | Pain gone | No pain | No pain | No pain | 1 case: no obvious change after 4 weeks of treatment 1 case: some effective |
| Kidney cancer 1 case | Pain relieved | Pain gone | No pain | No pain | No obvious change after 4 weeks of treatment |

Dose of the above cancer patients is taken once every two days, 150 mg/5% glucose aqueous solution is dripped intravenously. The dicycloplatin injection used was purchased from Beijing Xingda Technology System Co., Ltd. The specification was 50 mg/5 mL.

It has been found in the clinical treatment of tumor patients that dicycloplatin has a good effect on tumor-induced tissue edema and inflammation. In many cases of patients with brain metastases from lung cancer who took dicycloplatin orally or injected, it was found that after one to two weeks of dicycloplatin treatment, the tissue edema caused by cancer metastasis in the brain was basically eliminated. This shows that dicycloplatin has a good anti-inflammatory effect on inflammation. In many cases of liver cancer patients with hepatic tissue edema, after dicycliopla-tin infusion or oral administration for a period of time, the tissue edema significantly disappeared or reduced.

Example 22

Antiviral Effect of Other Components AA011 and VK021 Alone

Information of AA011 and VK021 was shown in Table 6.

| sample | Molecular weight | Weight (mg) | +DMSO (μl) | Staring concentration (μM) | Starting concentration (μg/ml) | Dilute gradient |
|---|---|---|---|---|---|---|
| AA011 | 309 | 16.4 | 531 | 1000 | 324 | 4 fold |
| VK021 | 309 | 30 | 971 | 1000 | 324 | 4 fold |

Figure 5:
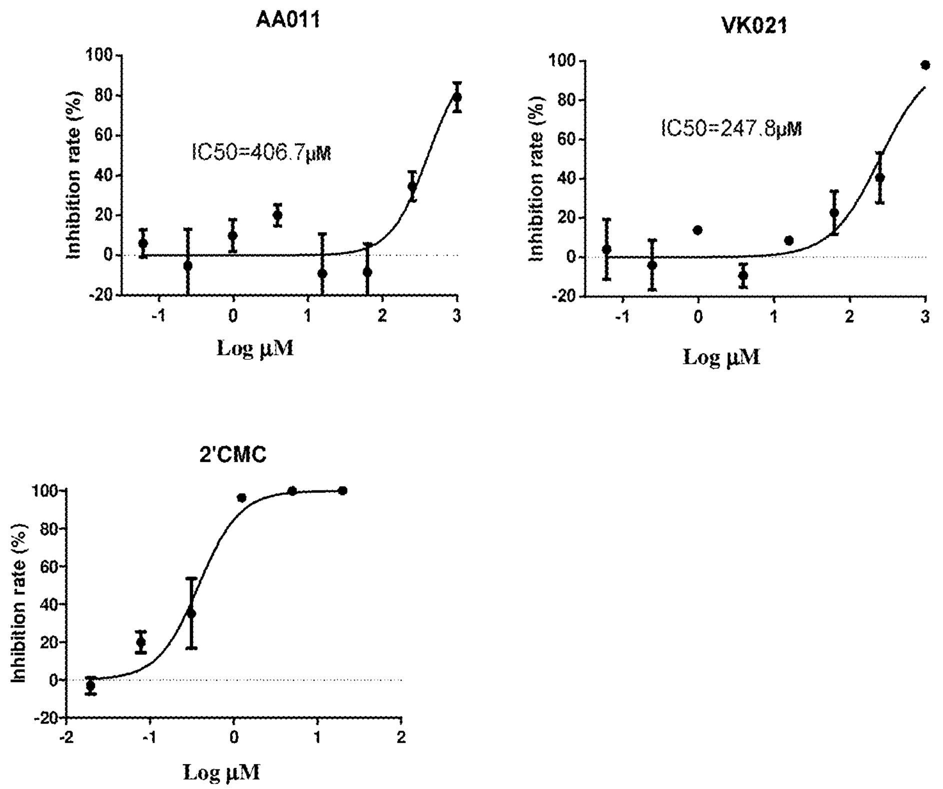
FIG. 5 shows the effect of AA011, VK021 and positive drugs on the virus.

As shown in FIG. 5, the antiviral effects of AA011, VK021 and positive drugs are shown in the figure below. The positive drug 2'CMC has a good antiviral effect, and the antiviral effect is better as the dose of the drug increases. Additive AA011 has a certain antiviral effect at 1000 μM and 250 μM concentration, and there is no obvious cytotoxicity at 1000 μM. Additive VK021 also has a certain antiviral effect at 1000 μM and 250 μM concentration, but has weak cytotoxicity at 1000 μM.

Example 23

In Vitro Efficacy of MD36792 and Combination Compositions Containing MD36792, AA011 and VK021 on HCV Virus Sample of MD36792, AA011 and VK021, and their test as shown in Table 7.

| sample | Molecular weight | Start concentration | Dilute dradient | CC50 | EC50 | SI |
|---|---|---|---|---|---|---|
| MD36792 | 500 | 200 μg/ml | 4 X | 69.4 | 15.62 | 4.44 |
| MD36792 | 500 | 200 μg/ml | 4 X | 24.82 | 4.43 | 5.60 |
| AA011 | 309 | 4000 μg/ml | | | | |
| VK021 | 309 | 4000 μg/ml | | | | |

Figure 6:
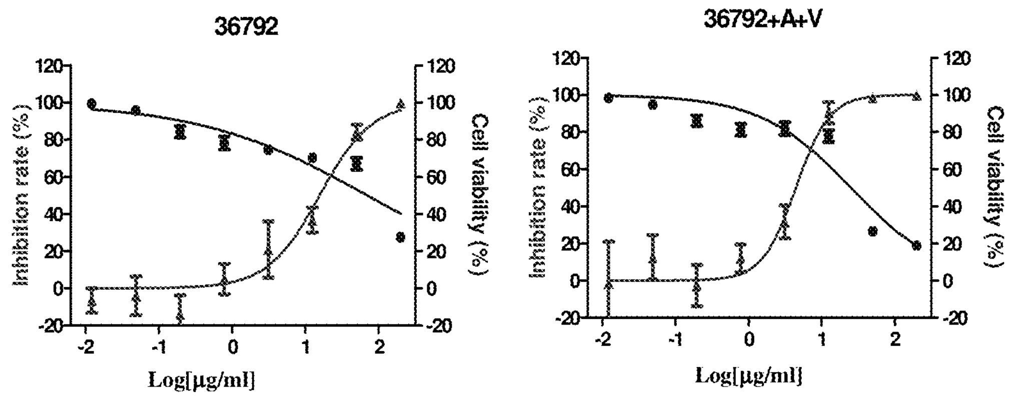
FIG. 6 shows the antiviral effect of combination composition of MD36792, AA011 (A in FIG. 6) and VK021 (V in FIG. 6).

Antivirus effect of MD36792, AA011 and VK021 was shown in FIG. 6.

The antiviral effect of the combination of MD36792 and AA011 was shown as A in FIG. 6, while MD36792 and VK021 was shown as V in FIG. 6. The EC50 of MD36792 alone is 15.62 μg/ml, the toxic CC50 to the cells is 69.4, and the selection index SI of the antiviral effect is 4.44. The selection index is relatively low, which can be considered to have a certain antiviral effect, but the toxicity to the cells is relatively large. The antiviral effects of MD36792 combined with AA011 and VK021 are EC50 of 4.43 μg/ml, CC50 of 24.82, and SI of 5.6. The mixed use of the three samples is more toxic to the cells and the selection index is not very large. The antiviral effect of the combined use of MD36792 alone has not significantly improved at the cellular level.

Example 24

Study of the Analgesic Effect of MD36792

(I) Experimental Materials, Animals and Equipment

Animals: 50 ICR mice, 18-22 g (Changsha Sleck Jingda Experimental Animal Company)

Reagent: Rotundine (manufactured by Guangzhou Baiyunshan Pharmaceutical).

Instrument: glass cover

Drug: MD36792

(II) Experimental Methods and Experimental Results

Experimental method: Animals were adaptively fed for 5 days, and the body weight of the mice was weighed. Using stratified random grouping, 50 mice were randomly divided into a total of 5 groups, distilled water used for the blank control group, i.e. model group, Rotundine used for the positive control group referring to 100 mg/kg, 1 mg/ml aqueous MD36792 solution used for low-dose group referring to 10 mg/kg, 2 mg/ml aqueous MD36792 solution used for medium-dose group referring to 20 mg/kg, and 4 mg/ml aqueous MD36792 solution used for high-dose group referring to 40 mg/kg,. The mice assigned to MD36792 group and the positive control group were given the corresponding drugs. After 1 hour of administration, the mice in each group were intraperitoneally injected with 0.8% acetic acid (0.2 mL/head). The twisting number of the mice were observed and recorded within 15 minutes.

TABLE 8

| Group | Sample Test | Mice Number | Dose (mg/kg) | weight Mean | weight SEM | Twisting Number Mean | Twisting Number SEM | P |
|---|---|---|---|---|---|---|---|---|
| A | Model group | 10 | 0 | 23.9 | 0.5 | 19.0 | 2.1 | |
| B | Rotundine Group | 10 | 100 | 23.9 | 0.3 | 2.8 | 1.2 | 0.000** |
| C | MD36792 Low dose | 10 | 10 | 23.5 | 0.5 | 15.2 | 3.6 | |
| D | MD36792 Middle dose | 10 | 20 | 24.0 | 0.4 | 14.8 | 2.2 | |
| E | MD36792 High dose | 10 | 40 | 23.6 | 0.4 | 8.7 | 3.1 | 0.009** |

Figure 7:
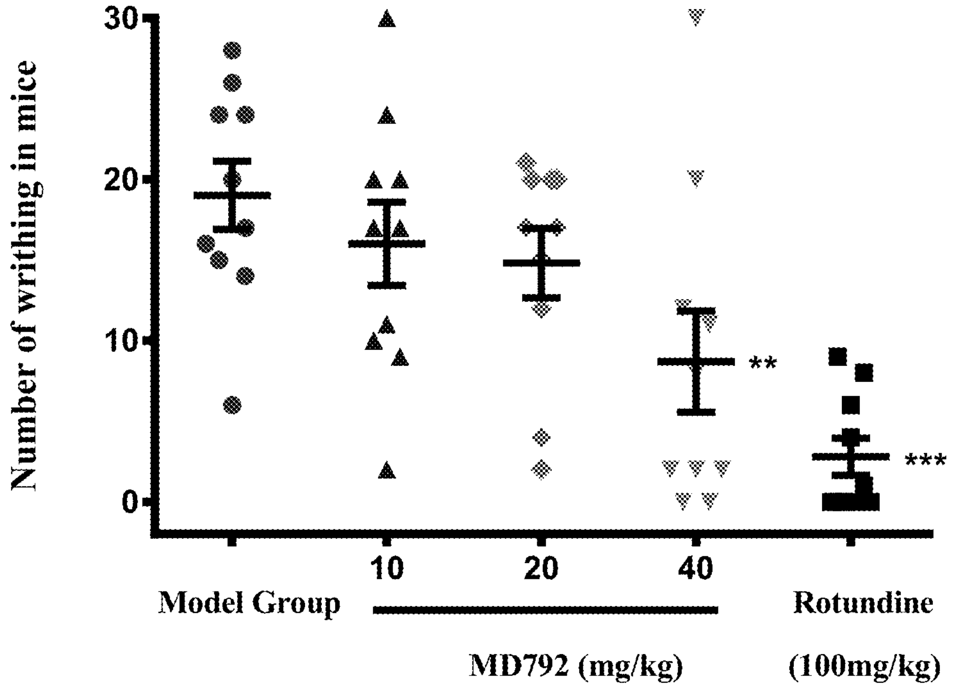
FIG. 7 shows the analgesic effect of MD36792.

* Compared with the model group (i.e., the blank control group), there is a statistically significant difference, $P < 0.05$**
* Compared with the model group (i.e., the blank control group), there is a statistically significant difference, $P < 0.01$ Within 15 minutes after intraperitoneal injection of 0.8% acetic acid, the average number of twisting in the model group reached 19 times. Compared with the model group, the MD36792 high-dose group (40 mg/kg) and the positive control group (Rotundine, 100 mg/kg) statistically significantly suppressed the number of writhing in mice (P=0.009 or P=0.000, respectively)). MD36792 is dose-independent in terms of analgesic effects as shown in FIG. 7.

Therefore, the classic acetic acid-induced model was used to evaluate the analgesic effect of the drugs. The above data, obtained from the model showed both MD36792 and the positive control drug Rotundine have significant analgesic effects.

What is claimed is:

1. A method of treating cancer pain, the method comprising administering an effective dose of dicycloplatin for treating the cancer pain to a patient in need thereof, wherein the patient has developed drug resistance to platinum anticancer drugs and is a cancer patient whose tumor is insensitive to dicycloplatin treatment.

2. The method according to claim 1, further comprising administering one or more active ingredients having an anticancer effect to the patient, wherein the one or more active ingredients having an anticancer effect are selected from non-platinum anticancer drugs.

3. The method according to claim 1, wherein the patient is a liver cancer patient.

4. The method according to claim 1, wherein the patient is a kidney cancer patient.

5. The method according to claim 1, wherein the patient has bone metastasis.

6. The method according to claim 1, wherein the patient has brain metastasis or bone cancer.

7. The method according to claim 1, wherein the patient is an advanced cancer patient.

8. The method according to claim 1, wherein the patient is an advanced liver cancer patient.

9. The method according to claim 1, wherein the dicycloplatin is administered to the patient orally.

10. The method according to claim 1, wherein the dicycloplatin is administered to the patient through injection.

11. The method according to claim 1, wherein the dicycloplatin is the only active ingredient for the treatment of cancer pain.

* * * * *